(12) United States Patent
Liu et al.

(10) Patent No.: US 11,008,360 B2
(45) Date of Patent: May 18, 2021

(54) INDOLEACETIC ACID DERIVATIVE AND PREPARATION METHOD AND PHARMACEUTICAL USE THEREOF

(71) Applicant: Institute of Chinese Materia Medica, China Academy of Chinese Medical Sciences, Beijing (CN)

(72) Inventors: An Liu, Beijing (CN); Jintang Cheng, Beijing (CN); Cong Guo, Beijing (CN); Jun Zhang, Beijing (CN); Chang Chen, Beijing (CN)

(73) Assignee: Institute of Chinese Materia Medica, China Academy of Chinese Medical Sciences, Beijing (CN)

( * ) Notice: Subject to any disclaimer, the term of this patent is extended or adjusted under 35 U.S.C. 154(b) by 0 days.

(21) Appl. No.: 16/620,015

(22) PCT Filed: May 15, 2018

(86) PCT No.: PCT/CN2018/086774
§ 371 (c)(1),
(2) Date: Dec. 6, 2019

(87) PCT Pub. No.: WO2018/223819
PCT Pub. Date: Dec. 13, 2018

(65) Prior Publication Data
US 2020/0095271 A1     Mar. 26, 2020

(30) Foreign Application Priority Data
Jun. 7, 2017   (CN) .......................... 201710421776.4

(51) Int. Cl.
*C07H 19/044*        (2006.01)
(52) U.S. Cl.
CPC ................................. *C07H 19/044* (2013.01)
(58) Field of Classification Search
None
See application file for complete search history.

(56) References Cited

FOREIGN PATENT DOCUMENTS

| CN | 1933830 A | 3/2007 |
|---|---|---|
| WO | 2016100281 A1 | 6/2016 |

OTHER PUBLICATIONS

Kai et al., Phytochemistry, vol. 68, 2007, pp. 2512-2522. (Year: 2007).*
International Search Report; State Intellectual Property Office of the P.R. China; International Application No. PCT/CN2018/086774; dated Aug. 8, 2018; 5 pages.

* cited by examiner

*Primary Examiner* — Traviss C McIntosh, III
(74) *Attorney, Agent, or Firm* — Taft Stettinius & Hollister LLP

(57) ABSTRACT

The present invention relates to an indoleacetic acid derivative and a preparation method and pharmaceutical use thereof. In particular, the present invention relates to a compound shown in general formula (I), a preparation method thereof, a pharmaceutical composition comprising the same, and a use thereof as a cough suppressant in treating a disease such as a cough. The definition of each substituent in the general formula (I) is the same as the definition in the specification.

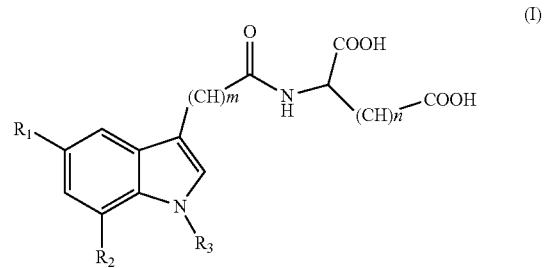

18 Claims, No Drawings

INDOLEACETIC ACID DERIVATIVE AND PREPARATION METHOD AND PHARMACEUTICAL USE THEREOF

CROSS-REFERENCE TO RELATED APPLICATIONS

This application is a U.S. National Phase of International PCT Application No. PCT/CN2018/086774 filed May 15, 2018, which claims the benefit of Chinese Patent Application Serial No. 201710421776.4 filed Jun. 7, 2017, the contents of each application are incorporated herein by reference in their entirety.

FIELD OF THE INVENTION

The present invention belongs to the field of medicine, and particularly relates to a novel indoleacetic acid derivatives, a preparation method and a pharmaceutical composition comprising the same, as well as a use thereof as an antitussive in the treatment of diseases such as cough.

BACKGROUND OF THE INVENTION

Cough and bronchial asthma are the two most common diseases of the respiratory system, which seriously affect people's life quality. Thus the development of antitussive and antiasthmatic drugs has received much attention.

At present, clinical antitussives can be classified into two main types: central and peripheral antitussives. Central cough medicines include methadone, codeine, morphine and the like, which are mostly used for reflexive dry cough, but have side effects clinically such as nausea, constipation, lethargy and addiction. Peripheral antitussives include lung-reducing drugs such as lupus, honey and syrup, or respiratory tract inhalation drugs such as compound tincture of benzoin, sodium chloride or eucalyptol.

According to the mechanism of action, asthma drugs can be divided into bronchodilators, anti-inflammatory asthma drugs and anti-allergic antiasthmatic drugs. Bronchodilators include theophyllines, inhaled anticholinergic and β2 receptor agonist. Theophyllines inhibit phosphodiesterase, directly increase the level of intracellular cyclic adenosine monophosphate/cyclic guanosine monophosphate (cAMP/cGMP), and relaxe smooth muscle. However, the safe range of theophylline is narrow, and blood concentration must be monitored, which brings certain difficulties to the clinical treatment. Inhaled anticholinergic drugs have a selective effect on airway smooth muscle, but the effect is slow. Non-selective β2 receptor agonist has a strong antiasthmatic effect. However, it has multiple side effects such as cardiac responses including tachycardia, palpitation and the like, which are related to the stimulation of cardiac β2 receptor, and can result in severe cardiac adverse reactions. Selective β2 receptor drugs such as salbutamol have side effects such as abnormal heartbeat, increased heart rate, and dizziness. Anti-inflammatory antiasthmatic has become the first-line drug among antiasthmatic drugs, and achieves a long-term prevention of asthma attacks by inhibiting airway inflammation. Glucocorticoid such as dexamethasone is currently the most common anti-inflammatory antiasthmatic. However, long-term administration of glucocorticoid can lead to osteoporosis and severe withdrawal reactions. Antiallergic antiasthmatic drugs include HI receptor blockers such as ketotifen; cell membrane stabilizers such as sodium cromoglycate; and leukotriene blockers, cysteinyl leukotrienes, and the like. The mechanism of action of these drugs is to block the mediators of mast cell release mediators by inhibiting immunoglobulin IgE, and to inhibit the increase of inflammatory cells such as eosinophils, macrophages and monocytes, and to exert anti-allergic effects and lightness degree of anti-inflammatory effect. However, its onset is slow and cannot be used in acute asthma attacks. It is only used to prevent asthma.

Therefore, there is still a need to develop a new and effective antitussive and antiasthmatic drug that can be effectively used in the treatment of diseases such as cough and bronchial asthma, as well as overcome the side effects existing in the prior art.

SUMMARY OF THE INVENTION

The inventors designed and synthesized a series of indoleacetic acid compounds. Studies have shown that these compounds have a good antitussive effect, and can be developed as an effective antitussive and antiasthmatic drug.

Accordingly, an object of the present invention is to provide a compound of formula (I), or a mesomer, racemate, enantiomer, diastereomer thereof, or a mixture thereof, or a pharmaceutically acceptable salt thereof,

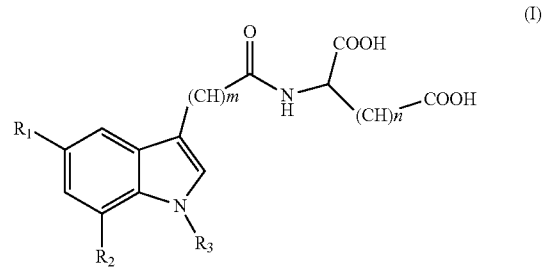

wherein,

R$_1$ is selected from the group consisting of hydrogen, halogen, hydroxy, amino, cyano, alkyl, alkoxy, haloalkyl, haloalkoxy and cycloalkyl;

R$_2$ is selected from the group consisting of hydrogen, halogen, alkyl, alkoxy, haloalkyl, haloalkoxy and cycloalkyl;

R$_3$ is selected from the group consisting of pentose and hexose;

n is an integer from 1 to 4; and m is an integer from 1 to 4.

In a preferred embodiment of the present invention, the compound of formula (I), or a mesomer, racemate, enantiomer, diastereomer thereof, or a mixture thereof, or a pharmaceutically acceptable salt thereof according to the present invention is a compound of formula (II), or a mesomer, racemate, enantiomer, diastereomer thereof, or a mixture thereof, or a pharmaceutically acceptable salt thereof,

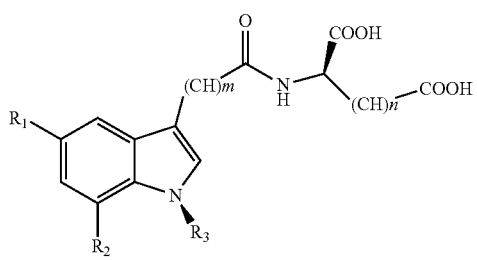

(II)

wherein, $R_1$, $R_2$, $R_3$, m and n are as defined in formula (I).

In another preferred embodiment of the present invention, the compound of formula (I), or a mesomer, racemate, enantiomer, diastereomer thereof, or a mixture thereof, or a pharmaceutically acceptable salt thereof according to the present invention, wherein $R_1$ is selected from the group consisting of hydrogen, halogen, alkyl, alkoxy, haloalkyl and haloalkoxy, preferably hydrogen, halogen, $C_1$-$C_6$ alkyl and $C_1$-$C_6$ alkoxy.

In another preferred embodiment of the present invention, the compound of formula (I), or a mesomer, racemate, enantiomer, diastereomer thereof, or a mixture thereof, or a pharmaceutically acceptable salt thereof according to the present invention, wherein $R_2$ is selected from the group consisting of hydrogen, halogen, $C_1$-$C_6$ alkyl and $C_1$-$C_6$ alkoxy.

In another preferred embodiment of the present invention, the compound of formula (I), or a mesomer, racemate, enantiomer, diastereomer thereof, or a mixture thereof, or a pharmaceutically acceptable salt thereof according to the present invention, wherein $R_3$ is pentose, preferably selected from the group consisting of ribose, deoxyribose and xylose, and more preferably D-ribose, D-deoxyribose and D-xylose.

In another preferred embodiment of the present invention, the compound of formula (I), or a mesomer, racemate, enantiomer, diastereomer thereof, or a mixture thereof, or a pharmaceutically acceptable salt thereof according to the present invention, wherein $R_3$ is hexose, preferably selected from the group consisting of glucose, fructose and galactose, and more preferably D-glucose, D-fructose and D-galactose.

In another preferred embodiment of the present invention, the compound of formula (I), or a mesomer, racemate, enantiomer, diastereomer thereof, or a mixture thereof, or a pharmaceutically acceptable salt thereof according to the present invention, wherein m is 1 or 2, and preferably m is 1.

In another preferred embodiment of the present invention, the compound of formula (I), or a mesomer, racemate, enantiomer, diastereomer thereof, or a mixture thereof, or a pharmaceutically acceptable salt thereof according to the present invention, wherein n is 1 or 2.

Typical compounds of the present invention include, but are not limited to:

| Compound No. | Structure and name |
|---|---|
| 1 | (2-(1-((2R,3R,4S,5S,6R)-3,4,5-trihydroxy-6-hydroxymethyl)tetrahydro-2H-pyran-2-yl)-1H-indol-3-yl)acetyl)-D-aspartic acid |
| 2 | (2-(1-((2R,3R,4S,5S,6R)-3,4,5-trihydroxy-6-hydroxymethyl)tetrahydro-2H-pyran-2-yl)-1H-indol-3-yl)acetyl)-D-glutamic acid |
| 3 | (2-(5-methyl-1-((2R,3R,4S,5S,6R)-3,4,5-trihydroxy-6-hydroxymethyl)tetrahydro-2H-pyran-2-yl)-1H-indol-3-yl)acetyl)-D-aspartic acid |

-continued

| Compound No. | Structure and name |
|---|---|
| 4 | 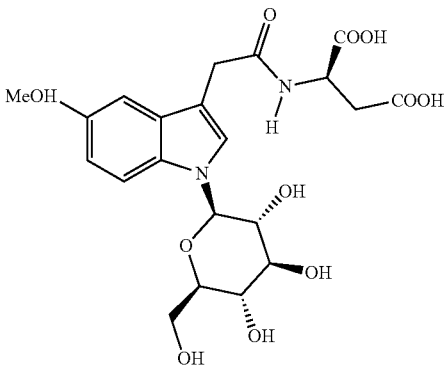 2-(5-methoxy-1-((2R,3R,4S,5S,6R)-3,4,5-trihydroxy-6-hydroxymethyl)tetrahydro-2H-pyran-2-yl)-1H-indol-3-yl)acetyl)-D-aspartic acid |
| 5 | 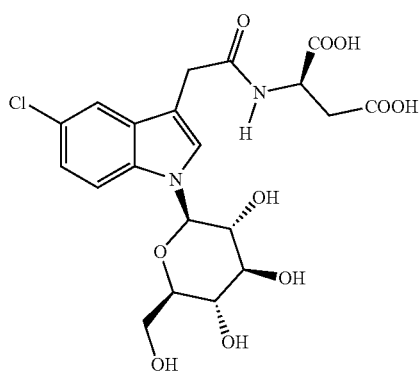 (2-(5-chloro-1-((2R,3R,4S,5S,6R)-3,4,5-trihydroxy-6-hydroxymethyl)tetrahydro-2H-pyran-2-yl)-1H-indol-3-yl)acetyl)-D-aspartic acid |
| 6 | 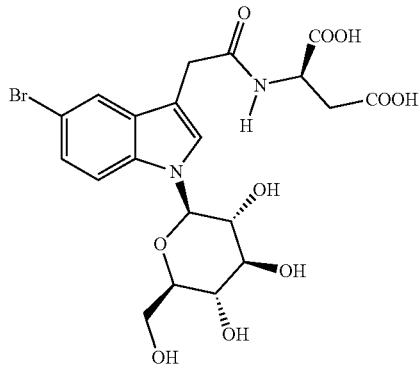 (2-(5-bromo-1-((2R,3R,4S,5S,6R)-3,4,5-trihydroxy-6-hydroxymethyl)tetrahydro-2H-pyran-2-yl)-1H-indol-3-yl)acetyl)-D-aspartic acid |

-continued

| Compound No. | Structure and name |
|---|---|
| 7 | 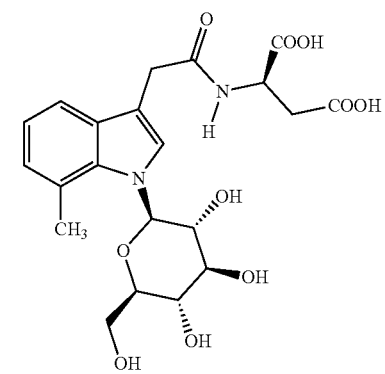 (2-(7-methyl-1-((2R,3R,4S,5S,6R)-3,4,5-trihydroxy-6-hydroxymethyl)tetrahydro-2H-pyran-2-yl)-1H-indol-3-yl)acetyl)-D-aspartic acid |
| 8 | 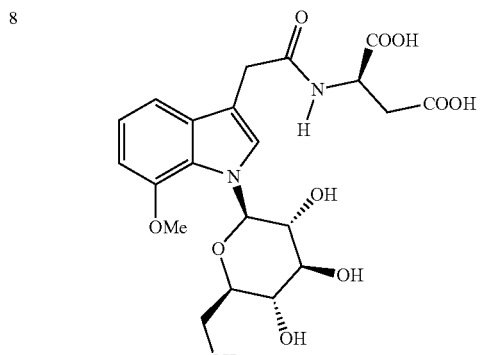 (2-(7-methoxy-1-((2R,3R,4S,5S,6R)-3,4,5-trihydroxy-6-hydroxymethyl)tetrahydro-2H-pyran-2-yl)-1H-indol-3-yl)acetyl)-D-aspartic acid |
| 9 | 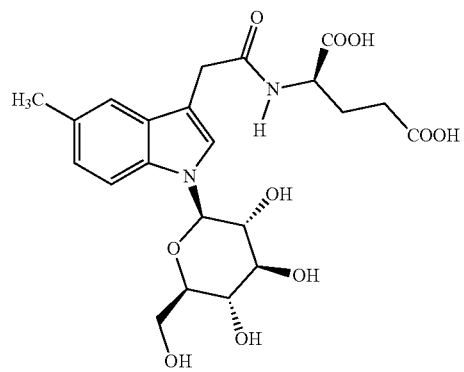 (2-(5-methyl-1-((2R,3R,4S,5S,6R)-3,4,5-trihydroxy-6-hydroxymethyl)tetrahydro-2H-pyran-2-yl)-1H-indol-3-yl)acetyl)-D-glutamic acid |

| Compound No. | Structure and name |
|---|---|
| 10 | 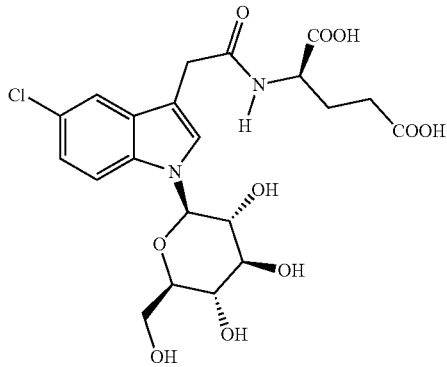<br>(2-(5-chloro-1-((2R,3R,4S,5S,6R)-3,4,5-trihydroxy-6-hydroxymethyl)tetrahydro-2H-pyran-2-yl)-1H-indol-3-yl)acetyl)-D-glutamic acid | or a mesomer, racemate, enantiomer, diastereomer thereof, or a mixture thereof, or a pharmaceutically acceptable salt thereof.

In another preferred embodiment of the present invention, the compound of formula (I), or a mesomer, racemate, enantiomer, diastereomer thereof, or a mixture thereof, or a pharmaceutically acceptable salt thereof according to the present invention, wherein the pharmaceutically acceptable salt is a basic addition salt, and preferably sodium salt, potassium salt, calcium salt, magnesium salt, tetramethyl quaternary ammonium salt, tetraethyl quaternary ammonium salt, methylamine salt, dimethylamine salt, trimethylamine salt, triethylamine salt or ethylamine salt.

The present invention further provides a method for preparing the compound of formula (I), or a mesomer, racemate, enantiomer, diastereomer thereof, or a mixture thereof, or a pharmaceutically acceptable salt thereof according to the present invention, comprising of the following step:

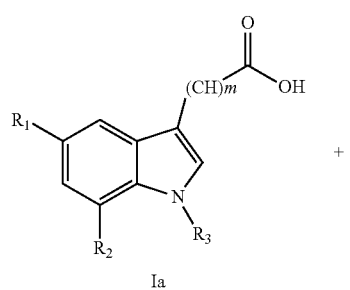
Ia

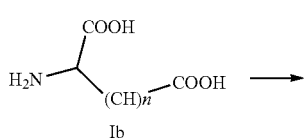
Ib

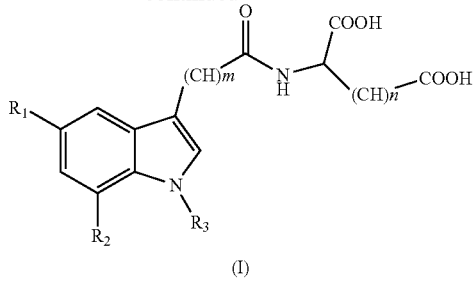
(I)

an intermediate Ia and an intermediate Ib are subjected to a coupling reaction in the presence of an activating reagent and a base to obtain the compound of formula (I);

wherein, the activating reagent is preferably DCC, and the base is preferably MMM.

In another aspect, the present invention relates to a pharmaceutical composition comprising the compound, or a mesomer, racemate, enantiomer, diastereomer thereof, or a mixture thereof, or a pharmaceutically acceptable salt thereof according to the present invention, as well as a pharmaceutically acceptable carrier.

In another aspect, the present invention relates to a use of the compound of formula (I), or a mesomer, racemate, enantiomer, diastereomer thereof, or a mixture thereof, or a pharmaceutically acceptable salt thereof according to the present invention, or the pharmaceutical composition comprising the same in the preparation of a medicament for the treatment of cough.

According to a conventional method in the art to which the present invention pertains, the compound of formula (I) of the present invention can form a basic addition salt of a pharmaceutically acceptable salt with a common base in the art, for example a salt formed with an alkali metal, amine or quaternary ammonium compound, and the base can be an inorganic or organic base. The salts formed with an alkali metal include, but are not limited to, sodium salt, lithium salt, potassium salt, calcium salt, magnesium salt and the like. The salts formed with an amine such as ammonia ($NH_3$), primary amine, secondary amine or tertiary amine include, but are not limited to, methylamine salt, dimethylamine salt, trimethylamine salt, triethylamine salt, ethylamine salt, ethanolamine salt, lysine salt, arginine salt and the like. The salts formed with a quaternary ammonium compound include, but are not limited to, tetramethyl quaternary ammonium salt, tetraethyl quaternary ammonium salt, choline salt and the like.

The pharmaceutical composition containing the active ingredient can be in a form suitable for oral administration, for example, a tablet, troche, lozenge, aqueous or oily suspension, dispersible powder or granule, emulsion, hard or soft capsule, syrup or elixir. An oral composition can be prepared according to any known method in the art for the preparation of pharmaceutical composition. Such composition can contain one or more ingredients selected from the group consisting of sweeteners, flavoring agents, colorants and preservatives, in order to provide a pleasing and palatable pharmaceutical formulation. The tablet contains the active ingredient in admixture with nontoxic, pharmaceutically acceptable carriers suitable for the preparation of tablets. These carriers may be inert carriers, such as calcium carbonate, sodium carbonate, lactose, calcium phosphate or sodium phosphate; granulating and disintegrating agents, such as microcrystalline cellulose, cross-linked sodium carboxymethyl cellulose, corn starch or alginic acid; binders, such as starch, gelatin, polyvinylpyrrolidone or acacia; and lubricants, such as magnesium stearate, stearic acid or talc. The tablet may be uncoated or coated by means of known techniques, which can mask drug taste or delay the disintegration and absorption of the active ingredient in the gastrointestinal tract, thereby providing sustained release over an extended period. For example, a water soluble taste masking material can be used, such as hydroxypropyl methylcellulose or hydroxypropyl cellulose, or an extended release material can be used, such as ethyl cellulose, or cellulose acetate butyrate.

An oral formulation can also be provided as hard gelatin capsules in which the active ingredient is mixed with an inert solid diluent, such as calcium carbonate, calcium phosphate or kaolin, or as soft gelatin capsules in which the active ingredient is mixed with a water soluble carrier such as polyethylene glycol or an oil medium such as peanut oil, liquid paraffin or olive oil.

An aqueous suspension contains the active ingredient in admixture with a carrier suitable for the preparation of aqueous suspension. Such carrier is a suspending agent, such as sodium carboxymethylcellulose, methylcellulose, hydroxypropylmethylcellulose, sodium alginate, polyvinylpyrrolidone and acacia; a dispersant or humectant, which can be a naturally occurring phosphatide such as lecithin, or a condensation product of an alkylene oxide with fatty acid such as polyoxyethylene stearate, or a condensation product of ethylene oxide with a long chain aliphatic alcohol such as heptadecaethyleneoxy cetanol, or a condensation product of ethylene oxide with part esters derived from fatty acids and hexitols such as polyoxyethylene sorbitol monooleate, or a condensation product of ethylene oxide with partial esters derived from fatty acids and hexitol anhydrides such as polyoxyethylene sorbitan monooleate. The aqueous suspension can also contain one or more preservatives, such as ethylparaben or n-propylparaben, one or more colorants, one or more flavoring agents, and one or more sweeteners such as sucrose, saccharin or aspartame.

An oil suspension can be formulated by suspending the active ingredient in a vegetable oil such as peanut oil, olive oil, sesame oil or coconut oil, or in a mineral oil such as liquid paraffin. The oil suspension can contain a thickener, such as beeswax, hard paraffin or cetyl alcohol. The above sweetener and flavoring agent can be added to provide a palatable formulation. These compositions can be preserved by adding an antioxidant, such as butylated hydroxyanisole or α-tocopherol.

The active ingredient in admixture with the dispersants or wetting agents, suspending agent or one or more preservatives can be prepared as a dispersible powder or granule suitable for the preparation of an aqueous suspension by adding water. Suitable dispersants or wetting agents and suspending agents are as described above. Additional carriers, such as sweetening agents, flavoring agents and coloring agents, can also be added. These compositions can be preserved by adding an antioxidant such as ascorbic acid.

The pharmaceutical composition of the present invention can also be in the form of an oil-in-water emulsion. The oil phase can be a vegetable oil such as olive oil or peanut oil, or a mineral oil such as liquid paraffin or a mixture thereof. Suitable emulsifying agent can be naturally occurring phosphatides, such as soy bean lecithin, and esters or partial esters derived from fatty acids and hexitol anhydrides such as sorbitan monooleate, and condensation products of said partial esters with ethylene oxide such as polyoxyethylene sorbitol monooleate. The emulsion can also contain a sweetener, flavoring agent, preservative and antioxidant. Syrup and elixir can be formulated with a sweetener, such as glycerol, propylene glycol, sorbitol or sucrose. Such formulations can also contain a moderator, a preservative, a colorant and an antioxidant.

The pharmaceutical composition can be in the form of a sterile injectable aqueous solution. The acceptable vehicles and solvents that can be employed include water, Ringer's solution and isotonic sodium chloride solution. The sterile injectable formulation can be a sterile injectable oil-in-water microemulsion in which the active ingredient is dissolved in the oil phase. For example, the active ingredient can be firstly dissolved in a mixture of soybean oil and lecithin, the oil solution is then introduced into a mixture of water and glycerol and processed to form a microemulsion. The injectable solution or microemulsion can be introduced into a patient's bloodstream by local bolus injection. Alternatively, it may be advantageous to administrate the solution or microemulsion in such a way as to maintain a constant circulating concentration of the compound of the present invention. In order to maintain such a constant concentration, a continuous intravenous delivery device can be utilized.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium. For this purpose, any blending fixed oils including synthetic mono- or di-glyceride can be employed. Moreover, fatty acids such as oleic acid can also be employed in the preparation of an injection.

It is well known to those skilled in the art that the dosage of a drug depends on a variety of factors including, but not limited to the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of formula (I) or the type of pharmaceutically acceptable salt thereof can be verified according to the traditional therapeutic regimens.

The present invention may contain a composition comprising the compound of formula (I) as an active ingredient, and a pharmaceutically acceptable carrier or excipient, which is formulated into a clinically acceptable formulation. The derivatives of the present invention can be used in combination with other active ingredients as long as they do not cause other adverse effects such as allergic reactions and the like. A combination therapy can be achieved by administrating the individual therapeutic components simultaneously, separately or sequentially.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, carboxy and alkoxycarbonyl.

The term "cycloalkyl" refers to a saturated or partially unsaturated monocyclic or polycyclic hydrocarbon substituent group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably 6 to 14 membered spiro cycloalkyl, and more preferably 7 to 10 membered spiro cycloalkyl. According to the number of the spiro atoms shared between the rings, the spiro cycloalkyl can be divided into mono-spiro cycloalkyl, di-spiro cycloalkyl, or poly-spiro cycloalkyl, and the spiro cycloalkyl is preferably a mono-spiro cycloalkyl or di-spiro cycloalkyl, and more preferably 4-membered/4-membered, 4-membered/5-membered, 4-membered/6-membered, 5-membered/5-membered or 5-membered/6-membered mono-spiro cycloalkyl. Non-limiting examples of spiro cycloalkyl include:

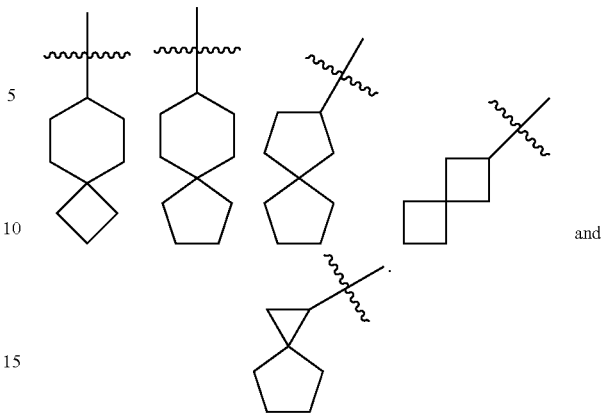

and

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated i-electron system. The fused cycloalkyl is preferably 6 to 14 membered fused cycloalkyl, and more preferably 7 to 10 membered fused cycloalkyl. According to the number of membered rings, the fused cycloalkyl can be divided into bicyclic, tricyclic, tetracyclic or polycyclic fused cycloalkyl, and the fused cycloalkyl is preferably bicyclic or tricyclic fused cycloalkyl, and more preferably 5-membered/5-membered or 5-membered/6-membered bicyclic fused cycloalkyl. Non-limiting examples of fused cycloalkyl include:

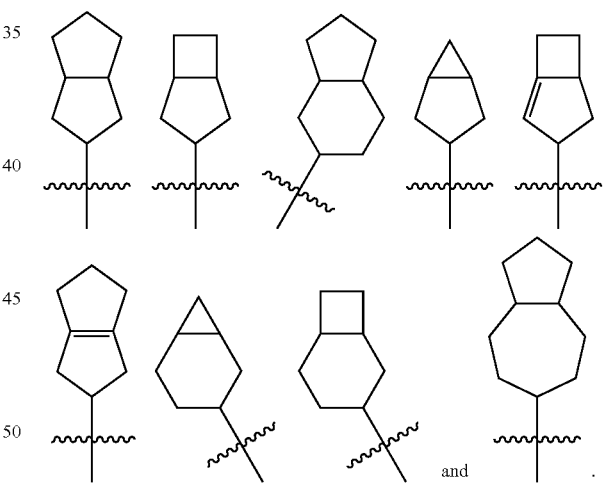

and

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated π-electron system. The bridged cycloalkyl is preferably 6 to 14 membered bridged cycloalkyl, and more preferably 7 to 10 membered bridged cycloalkyl. According to the number of membered rings, the bridged cycloalkyl can be divided into bicyclic, tricyclic, tetracyclic or polycyclic bridged cycloalkyl, and the bridged cycloalkyl is preferably bicyclic, tricyclic or tetracyclic bridged cycloalkyl, and more preferably bicyclic or tricyclic bridged cycloalkyl. Non-limiting examples of bridged cycloalkyls include:

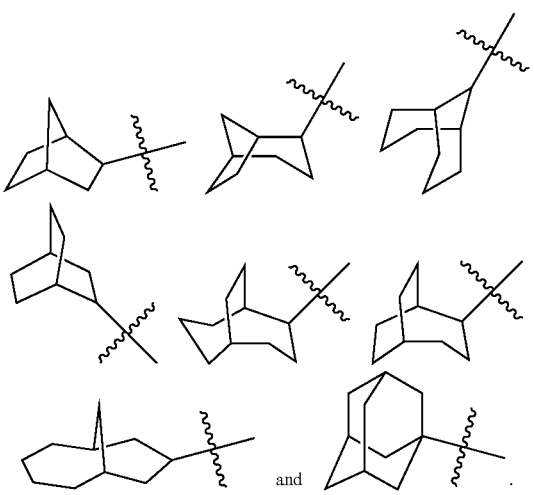

The ring of cycloalkyl can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, oxo, carboxy and alkoxycarbonyl.

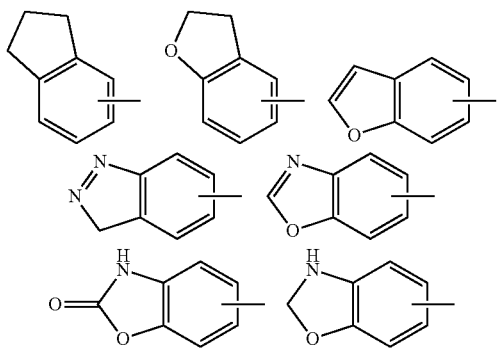

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio, carboxy and alkoxycarbonyl.

The term "haloalkyl" refers to an alkyl group substituted by one or more halogens, wherein the alkyl is as defined above.

The term "haloalkoxy" refers to an alkoxy group substituted by one or more halogens, wherein the alkoxy is as defined above.

The term "hydroxy" refers to an —OH group.

The term "halogen" refers to fluorine, chlorine, bromine or iodine.

The term "amino" refers to a —NH$_2$ group.

The term "cyano" refers to a —CN group.

The term "carboxy" refers to a —C(O)OH group.

The term "carboxylate group" refers to a —C(O)O(alkyl) or —C(O)O(cycloalkyl) group, wherein the alkyl is as defined above.

The term "acyl" refers to a compound containing a —C(O)R group, wherein R is alkyl, cycloalkyl, aryl or heteroaryl.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

Synthesis Method of the Compound of the Present Invention

In order to achieve the object of the present invention, the present invention applies the following technical solutions.

The method for preparing the compound of formula (I) of the present invention or a salt thereof is as shown in Scheme 1.

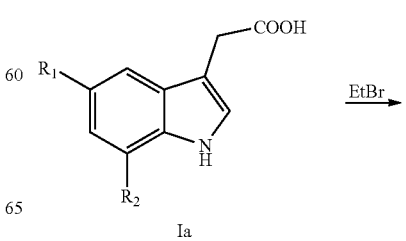

Scheme 1

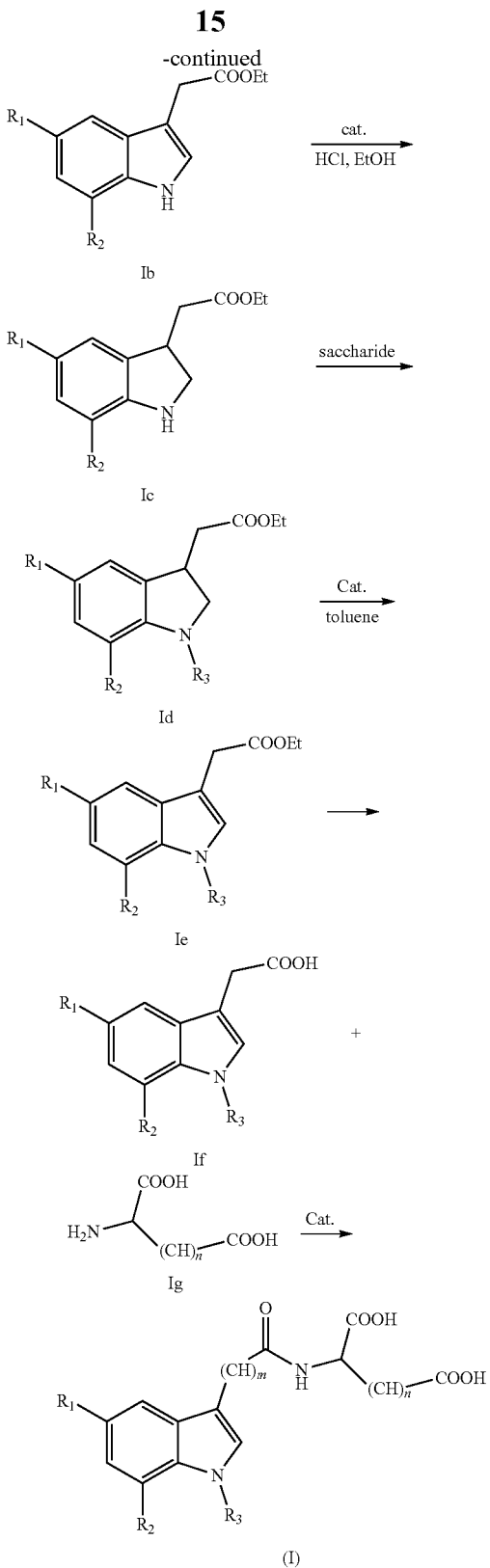

Step 1: compound 1a is reacted with bromoethane under an alkaline condition in a solvent to obtain compound 1b, the reagent that provides an alkaline condition is preferably potassium carbonate, and the solvent is preferably DMF;

Step 2: compound 1b is subjected to an oxidation reaction in a solution of hydrochloric acid in ethanol in the presence of a catalyst to obtain compound 1c, and the catalyst is preferably pyridinium-borane;

Step 3: compound 1c and the corresponding saccharide are heated to reflux in an alcohol solvent to obtain compound 1d, and the alcohol solvent is preferably ethanol;

Step 4: compound 1d is subjected to a reduction reaction in toluene in the presence of a catalyst to obtain compound 1e, and the catalyst is preferably DDQ;

Step 5: compound 1e is hydrolyzed under an alkaline condition to obtain compound 1f, and the reagent that provides an alkaline condition is preferably NaOH;

Step 6: compound 1f and compound 1 g are subjected to a coupling reaction in a solvent in the presence of a base and a catalyst to obtain the compound of formula (I), the solvent is preferably THF, the base is preferably N-methylmorpholine, and the catalyst is preferably DCC.

The present invention will be further described with reference to the following examples, but the examples should not be considered as limiting the scope of the present invention.

The structures of the compounds were identified by nuclear magnetic resonance (NMR) and/or mass spectrometry (MS). NMR shifts (δ) are given in $10^{-6}$ (ppm). NMR is determined by a Bruker dps600 machine. The solvents for determination are deuterated-dimethyl sulfoxide (DMSO-$d_6$), deuterated-chloroform ($CDCl_3$) and deuterated-methanol ($CD_3OD$), and the internal standard is tetramethylsilane (TMS).

MS is determined by a 1100 Series LC/MSD Trap(ESI) mass spectrometer (manufacturer: Agilent).

Preparative liquid chromatography is carried out on a lc3000 high performance liquid chromatograph and a lc6000 high performance liquid chromatograph (manufacturer: Beijing Chuangxintongheng Science and Technology Co., Ltd.).

HPLC is determined on a Shimadzu LC-20AD high pressure liquid chromatograph (Agilent TC-C18 250×4.6 mm 5vm chromatographic column) and a Shimadzu LC-2010AHT high pressure liquid chromatograph (Phenomenex C18 250×4.6 mm 5 um chromatographic column).

The average kinase inhibition rates and $IC_{50}$ values are determined by a multifunctional Cytation3 ELIASA (Bioteck Co., USA).

Qingdao Haiyang Chemical GF254 silica gel plate is used as the thin-layer silica gel chromatography (TLC) plate. The dimension of the silica gel plate used in TLC is 0.15 mm to 0.2 mm, and the dimension of the silica gel plate used in product purification is 0.4 mm to 0.5 mm.

Qingdao Haiyang 100 to 200 mesh silica gel and 200 to 300 mesh silica gel are generally used as a carrier for column chromatography.

The known starting materials of the present invention can be prepared by the known methods in the art, or can be purchased from companies such as WHmall, Innochem, Sigma, Energy Chemical and the like.

Unless otherwise stated, the reactions can be carried out under argon atmosphere or nitrogen atmosphere.

Unless otherwise stated, the solution refers to an aqueous solution.

Unless otherwise stated, the reaction temperature is room temperature from 20° C. to 30° C.

The reaction process in the examples is monitored by thin layer chromatography (TLC). The developing solvent system used includes: A: dichloromethane and methanol system, B: n-hexane and ethyl acetate system, C: petroleum ether and ethyl acetate system, D: acetone. The ratio of the volume of the solvent can be adjusted according to the polarity of the compounds.

The eluent system in column chromatography and the developing solvent system in thin layer chromatography for purification of the compounds include: A: dichloromethane and methanol system, B: n-hexane and ethyl acetate system, C: petroleum ether and ethyl acetate system. The ratio of the volume of the solvent can be adjusted according to the polarity of the compounds, and a small quantity of alkaline reagent such as triethylamine or acidic reagent such as acetic acid can also be added for adjustment.

Example 1 Preparation of (2-(1-(((2R,3R,4S,5S,6R)-3,4,5-trihydroxy-6-(hydroxymethyl)tetrahydro-2H-pyran-2-yl)-1H-indol-3-yl)acetyl)-D-aspartic acid

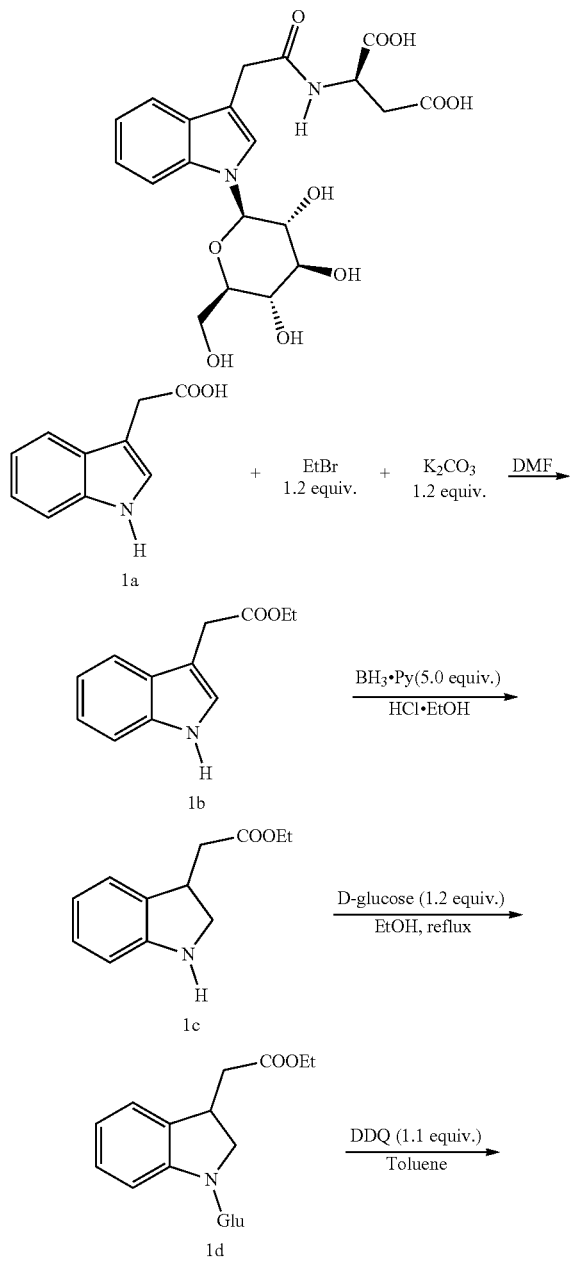

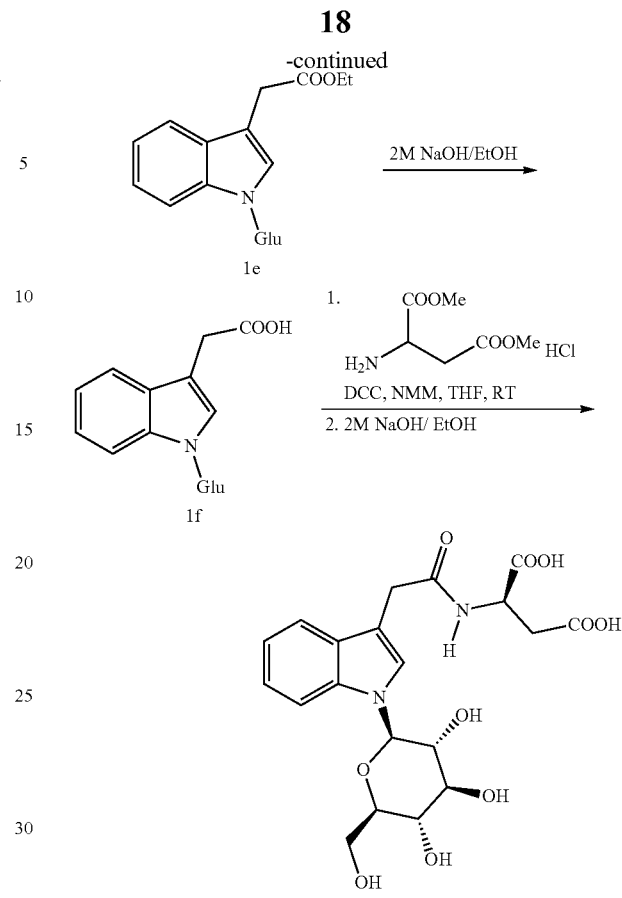

Step 1: Preparation of ethyl 2-(1H-indol-3-yl)acetate (1b)

2.0 g of indoleacetic acid was dissolved in 20 ml of DMF, and then $K_2CO_3$ (1.2 equivalent) was added thereto. The resulting mixture was stirred at room temperature for 30 minutes, and then added slowly with EtBr (1.2 equivalent) dropwise. After completion of the addition, the reaction mixture was stirred and refluxed for 4 hours. The reaction solution was then filtered. The filtrate was concentrated under reduced pressure. The residues were purified by column chromatography with petroleum ether:ethyl acetate 5:1 as the eluent to obtain the compound 1b (2.17 g, yield: 94%).

$^1$H-NMR (600 MHz): δ 8.28 (1H, brs, N—H), 7.66 (1H, d, J=7.8 Hz), 7.29 (1H, d, J=8.1 Hz), 7.22 (1H, t, J=7.5 Hz), 7.17 (1H, t, J=7.2 Hz), 7.04 (1H, s), 4.21 (2H, q, J=7.1 Hz), 3.81 (2H, s), 1.30 (1H, t, J=7.1 Hz). $^{13}$C-NMR (150 MHz): δ 172.4, 136.0, 127.0, 123.3, 122.0, 119.5, 118.8, 111.3, 108.0, 60.8, 31.4, 14.1.

Step 2: Preparation of ethyl 2-(indolin-3-yl)acetate (1c)

2.17 g of compound 1b was dissolved in 10 ml of a mixed solution of concentrated hydrochloric acid-ethanol (1:1), and slowly added with 5.0 equivalent of pyridinium-borane ($BH_3$.Py) solution at 0° C. The reaction solution was warmed to room temperature, and stirred for 1 hour. The reaction solution was concentrated under reduced pressure. The residues were added with 60 ml of 10% sodium carbonate aqueous solution to adjust the pH to 8, and extracted with 80 ml of ethyl acetate for three times. The ethyl acetate layer was separated, and purified by column chromatography with petroleum ether:ethyl acetate 5:1 as the eluent to obtain the title compound 1c (0.87 g, yield: 40%).

$^1$H-NMR (600 MHz): δ 7.09 (1H, d, J=7.3 Hz), 7.05 (1H, t, J=7.6 Hz), 6.72 (1H, t, J=7.4 Hz), 6.65 (1H, d, J=7.8 Hz), 4.18 (2H, q, J=7.1 Hz), 3.77 (1H, t, J=8.8 Hz), 3.73 (1H, m), 3.28 (1H, dd, J=8.9, 6.7 Hz), 2.77 (1H, dd, J=21.2, 10.6 Hz), 2.57 (1H, dd, J=16.0, 9.1 Hz), 1.28 (1H, t, J=7.1 Hz).

$^{13}$C-NMR (150 MHz): δ 172.5, 151.2, 131.1, 127.8, 123.7, 118.9, 109.9, 60.6, 53.2, 39.0, 38.3, 14.7.

Step 3: Preparation of ethyl 2-(1-((2R,3R,4S,5S,6R)-3,4,5-trihydroxy-6-(hydroxymethyl)tetrahydro-2H-pyran-2-yl)indolin-3-yl)acetate (1d)

0.87 g of compound 1c was dissolved in 5 ml of anhydrous ethanol. The reaction solution was added with D-glucose (1.2 equivalent), and refluxed for 5 hours. The reaction solution was filtered. The filtrate was purified by silica gel column chromatography with dichloromethane:methanol 10:1 as the eluent to obtain the compound 1d (0.96 g, yield: 62%).

$^1$H-NMR (600 MHz): A mixture of diastereomers in a ratio of 1:1.

δ 7.06 (2H, overlapping peak), 6.69 (2H, overlapping peak), 4.82 (1H, d, J=8.9 Hz), 4.18 (2H, m), 3.93 (1H, t, J=8.8 Hz), 3.80 (1H, m), 3.67 (2H, m), 3.54 (2H, m), 3.45 (1H, dd, J=9.1, 2.7 Hz), 3.35 (2H, overlapping peak), 2.94 (1H, dd, J=16.2, 5.2 Hz), 2.63 (1H, m), 1.29 (3H, t, J=7.1 Hz).

δ 7.06 (2H, overlapping peak), 6.69 (2H, overlapping peak), 4.82 (1H, d, J=8.9 Hz), 4.18 (2H, m), 3.84 (1H, t, J=9.1 Hz), 3.80 (1H, m), 3.67 (2H, m), 3.54 (2H, m), 3.34 (3H, overlapping peak), 2.63 (1H, m), 2.55 (1H, dd, J=16.2, 9.3 Hz), 1.25 (3H, t, J=7.1 Hz).

$^{13}$C-NMR (150 MHz): δ 174.3, 151.6, 133.8, 129.0, 125.3, 120.0, 109.4, 86.9, 79.3, 79.2, 72.1, 71.6, 62.7, 61.7, 53.3, 40.9, 38.1, 14.6.

δ 174.1, 151.2, 133.4, 128.8, 124.4, 119.9, 109.4, 86.7, 79.3, 79.2, 72.1, 71.6, 62.7, 61.6, 52.5, 39.6, 38.0, 14.5.

Step 4: Preparation of ethyl 2-(1-((2R,3R,4S,5S,6R)-3,4,5-trihydroxy-6-(hydroxymethyl)tetrahydro-2H-pyran-2-yl)-1H-indol-3-yl)acetate (1e)

0.96 g of compound 1d was dissolved in 5 ml of toluene. The reaction solution was added with 1.1 equivalent of DDQ, and stirred at room temperature for 24 hours. The reaction solution was filtered. The filtrate was purified by silica gel column chromatography with dichloromethane:methanol 19:1 as the eluent to obtain the compound 1e (0.36 g, yield: 38%).

$^1$H-NMR (600 MHz): δ 7.54 (2H, t, J=8.7 Hz), 7.38 (1H, s), 7.20 (1H, t, J=8.1 Hz), 7.10 (1H, t, J=7.8 Hz), 5.45 (1H, d, J=9.0 Hz), 4.17 (2H, q, J=7.1 Hz), 3.91 (2H, dt, J=12.2, 5.6 Hz), 3.78 (2H, s), 3.72 (1H, dd, J=12.2, 5.7 Hz), 3.60 (2H, m), 3.52 (1H, m), 1.27 (3H, t, J=7.1 Hz).

$^{13}$C-NMR (150 MHz): δ 174.1, 138.3, 129.5, 125.6, 123.0, 120.8, 120.0, 111.5, 110.0, 87.0, 80.5, 78.7, 73.7, 71.1, 62.7, 61.7, 31.8, 14.6.

Step 5: Preparation of 2-(1-((2R,3R,4S,5S,6R)-3,4,5-trihydroxy-6-(hydroxymethyl)tetrahydro-2H-pyran-2-yl)-1H-indol-3-yl)acetic acid (1f)

0.36 g of compound 1e was dissolved in a sodium hydroxide-ethanol solution (2M), and the reaction solution was refluxed for 1 hour. After completion of the reaction, the pH was adjusted to 1-2 with hydrochloric acid, and the reaction solution was extracted with 20 ml of ethyl acetate twice. The organic phases were combined, dried over anhydrous sodium sulfate, and filtered. The filtrate was concentrated under reduced pressure. The residues were purified by silica gel column chromatography with dichloromethane:methanol 3:1 as the eluent to obtain the compound 1f (0.31 g, yield: 95%).

$^1$H-NMR (600 MHz): δ 7.53 (1H, d, J=7.8 Hz), 7.49 (1H, d, J=7.6 Hz), 7.37 (1H, s), 7.18 (1H, t, J=7.0 Hz), 7.08 (1H, t, J=7.0 Hz), 5.46 (1H, d, J=8.7 Hz), 3.92 (1H, t, 8.6), 3.88 (1H, d, 11.9), 3.78-3.76 (2H, s), 3.73-3.68 (2H, m), 3.65-3.60 (2H, m), 3.52 (1H, t, 8.9).

$^{13}$C-NMR (150 MHz): δ 174.5, 138.2, 129.5, 125.5, 122.8, 121.1, 119.5, 111.4, 109.8, 86.6, 80.3, 78.9, 73.8, 71.8, 62.5, 31.6.

Step 6: Preparation of (2-(1-((2R,3R,4S,5S,6R)-3,4,5-trihydroxy-6-(hydroxymethyl)tetrahydro-2H-pyran-2-yl)-1H-indol-3-yl)acetyl)-D-aspartic acid (1)

0.31 g of compound 1f was dissolved in 4 ml of tetrahydrofuran. The reaction solution was added with methyl D-aspartate (0.282 g, 1.5 equivalents), DCC (0.294 g, 1.5 equivalents) and N-methylmorpholine (0.141 g, 1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 1 as a white solid (0.33 g, yield: 80%).

$^1$H-NMR (600 MHz): δ 7.52 (2H, dd, J=8.0, 3.2 Hz), 7.36 (1H, s), 7.17 (1H, t, J=7.7 Hz), 7.07 (1H, t, J=7.4 Hz), 5.43 (1H, d, J=9.0 Hz), 4.75 (1H, t, J=4.8 Hz), 3.92 (1H, m), 3.86 (1H, dd, J=12.1, 1.7 Hz), 3.70 (3H, m), 3.58 (2H, m), 3.51 (1H, m), 2.81 (2H, m).

$^{13}$C-NMR (150 MHz): δ 174.3, 174.2, 174.1, 138.3, 129.4, 125.7, 123.2, 121.1, 119.8, 111.4, 110.3, 86.3, 80.2, 78.7, 73.6, 71.4, 62.3, 49.9, 36.9, 33.3.

Example 2 Preparation of (2-(1-((2R,3R,4S,5S,6R)-3,4,5-trihydroxy-6-(hydroxymethyl)tetrahydro-2H-pyran-2-yl)-1H-indol-3-yl)acetyl)-D-glutamic acid

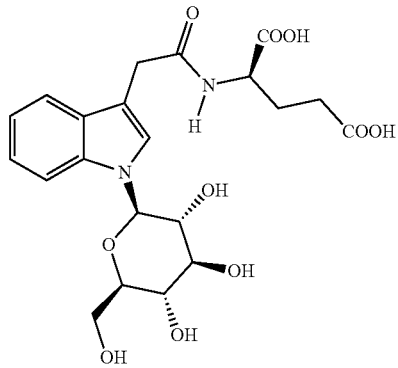

2

-continued

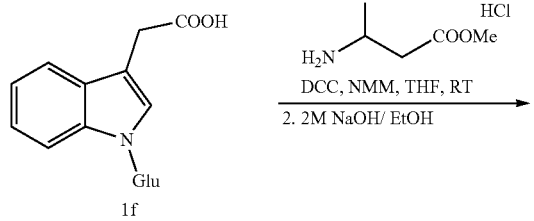

1f

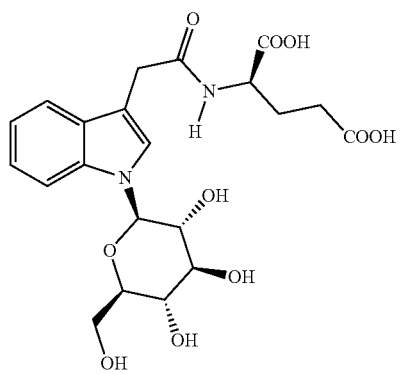

2

Step 1: Preparation of (2-(1-((2R,3R,4S,5S,6R)-3,4,5-trihydroxy-6-(hydroxymethyl)tetrahydro-2H-pyran-2-yl)-1H-indol-3-yl)acetyl)-D-glutamic acid (2)

0.31 g of compound 1f was dissolved in 4 ml of tetrahydrofuran. The reaction solution was added with methyl D-glutamate (0.306 g, 1.5 equivalents), DCC (0.294 g, 1.5 equivalents) and N-methylmorpholine (0.141 g, 1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the compound 2 as a white solid (0.36 g, yield: 80%).

$^1$H-NMR (600 MHz): δ 7.54 (2H, dd, J=11.4, 7.9 Hz), 7.37 (1H, s), 7.17 (1H, m), 7.09 (1H, m), 5.45 (1H, m), 4.47 (1H, m), 3.94 (1H, dd, J=16.1, 8.1 Hz), 3.86 (1H, d, J=12.1 Hz), 3.71 (3H, m), 3.60 (3H, m), 2.38 (2H, m), 2.16 (1H, m), 1.94 (1H, m).

$^{13}$C-NMR (150 MHz): δ 176.6, 175.2, 174.8, 138.5, 129.7, 126.1, 123.3, 1281.2, 119.9, 111.6, 110.7, 86.7, 80.5, 78.7, 73.8, 71.5, 62.9, 49.5, 33.4, 31.3, 27.8.

Example 3 Preparation of (2-(5-methyl-1-((2R,3R,4S,5S,6R)-3,4,5-trihydroxy-6-(hydroxymethyl)tetrahydro-2H-pyran-2-yl)-1H-indol-3-yl)acetyl)-D-aspartic acid

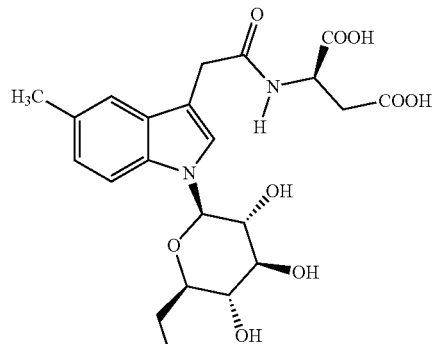

3

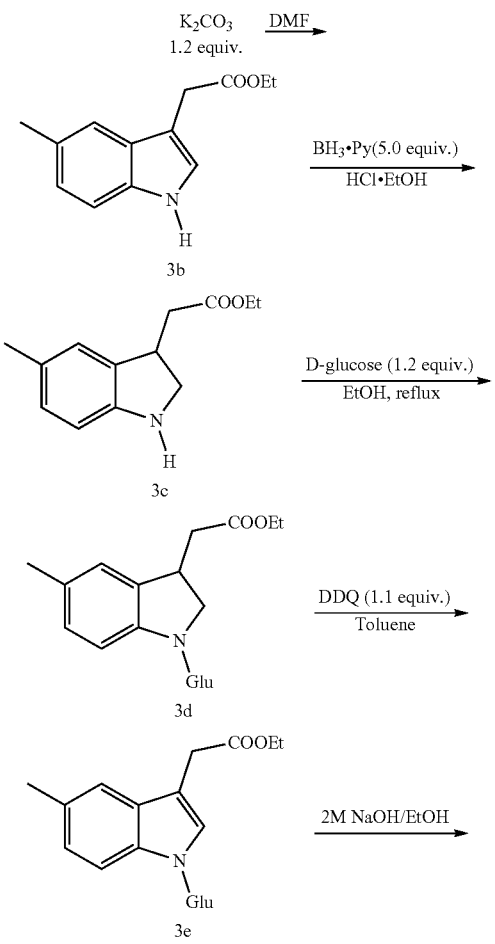

-continued

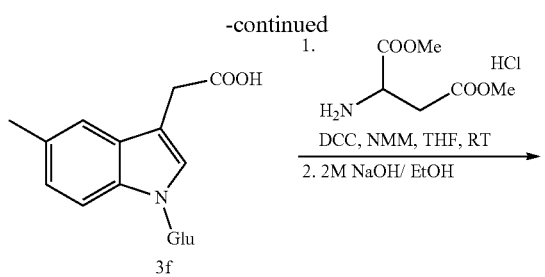

3f

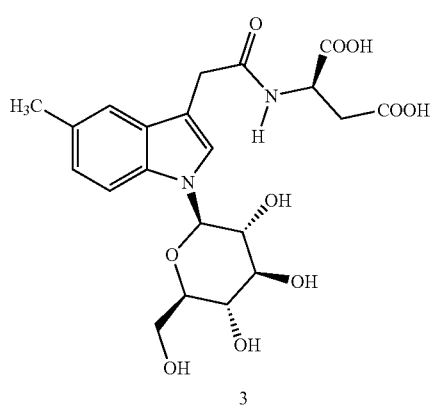

3

Step 1: Preparation of ethyl 2-(5-methyl-1H-indol-3-yl)acetate (3b)

2.0 g of 5-methylindoleacetic acid was dissolved in 20 ml of DMF, and then $K_2CO_3$ (1.2 equivalent) was added thereto. The resulting mixture was stirred at room temperature for 30 minutes, and then added slowly with EtBr (1.2 equivalent) dropwise. After completion of the addition, the reaction mixture was stirred and refluxed for 4 hours. The reaction solution was then filtered, and the filtrate was concentrated under reduced pressure. The residues were purified by column chromatography with petroleum ether: ethyl acetate 5:1 as the eluent to obtain the compound 3b (2.18 g, yield: 95%).

Step 2: Preparation of ethyl 2-(5-methylindolin-3-yl)acetate (3c)

2.18 g of compound 3b was dissolved in 10 ml of a mixed solution of concentrated hydrochloric acid-ethanol (1:1), and slowly added with 5.0 equivalent of pyridinium-borane ($BH_3.Py$) solution at 0° C. The reaction solution was warmed to room temperature, and stirred for 1 hour. The reaction solution was concentrated under reduced pressure. The residues were added with 60 ml of 10% sodium carbonate aqueous solution to adjust the pH to 8, and extracted with 80 ml of ethyl acetate for three times. The ethyl acetate layer was separated, and purified by column chromatography with petroleum ether:ethyl acetate 5:1 as the eluent to obtain the title compound 3c (1.16 g, yield: 53%).

Step 3: Preparation of ethyl 2-(1-((2R,3R,4S,5 S,6R)-3,4,5-trihydroxy-6-(hydroxymethyl)tetrahydro-2H-pyran-2-yl) 5-methylindolin-3-yl)acetate (3d)

1.16 g of compound 3c was dissolved in 5 ml of anhydrous ethanol. The reaction solution was added with D-glucose (1.2 equivalent), and refluxed for 5 hours. The reaction solution was filtered. The filtrate was purified by silica gel column chromatography with dichloromethane:methanol 10:1 as the eluent to obtain the compound 3d (1.20 g, yield: 65%).

Step 4: Preparation of ethyl 2-(1-((2R,3R,4S,5 S,6R)-3,4,5-trihydroxy-6-(hydroxymethyl)tetrahydro-2H-pyran-2-yl) 5-methyl-1H-indol-3-yl)acetate (3e)

1.20 g of compound 3d was dissolved in 5 ml of toluene. The reaction solution was added with 1.1 equivalent of DDQ, and stirred at room temperature for 24 hours. The reaction solution was filtered. The filtrate was purified by silica gel column chromatography with dichloromethane:methanol 19:1 as the eluent to obtain the compound 3e (0.51 g, yield: 43%).

Step 5: Preparation of 2-(1-((2R,3R,4S,5 S,6R)-3,4,5-trihydroxy-6-(hydroxymethyl)tetrahydro-2H-pyran-2-yl)-5-methyl-1H-indol-3-yl)acetic acid (3f)

0.51 g of compound 3e was dissolved in a sodium hydroxide-ethanol solution (2M), and the reaction solution was refluxed for 1 hour. After completion of the reaction, the pH was adjusted to 1-2 with hydrochloric acid, and the reaction solution was extracted with 20 ml of ethyl acetate twice. The organic phases were combined, dried over anhydrous sodium sulfate, and filtered. The filtrate was concentrated under reduced pressure. The residues were purified by silica gel column chromatography with dichloromethane:methanol 3:1 as the eluent to obtain the compound 3f (0.43 g, yield: 92%).

Step 6: Preparation of (2-(5-methyl-1-((2R,3R,4S,5S,6R)-3,4,5-trihydroxy-6-hydroxymethyl)tetrahydro-2H-pyran-2-yl)-1H-indol-3-yl)acetyl)-D-aspartic acid (3)

0.43 g of compound 3f was dissolved in 4 ml of tetrahydrofuran. The reaction solution was added with methyl D-aspartate (1.5 equivalents), DCC (1.5 equivalents) and N-methylmorpholine (1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 3 as a white solid (0.50 g, yield: 85%).

Example 4 Preparation of (2-(5-methoxy-1-((2R,3R,4S,5S,6R)-3,4,5-trihydroxy-6-hydroxymethyl)tetrahydro-2H-pyran-2-yl)-1H-indol-3-yl)acetyl)-D-aspartic acid

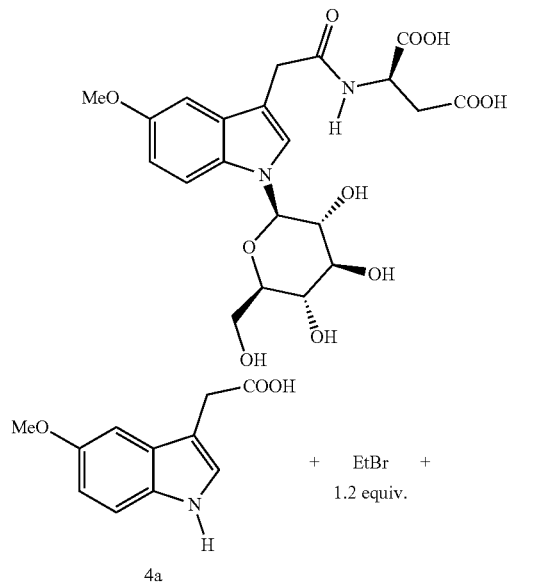

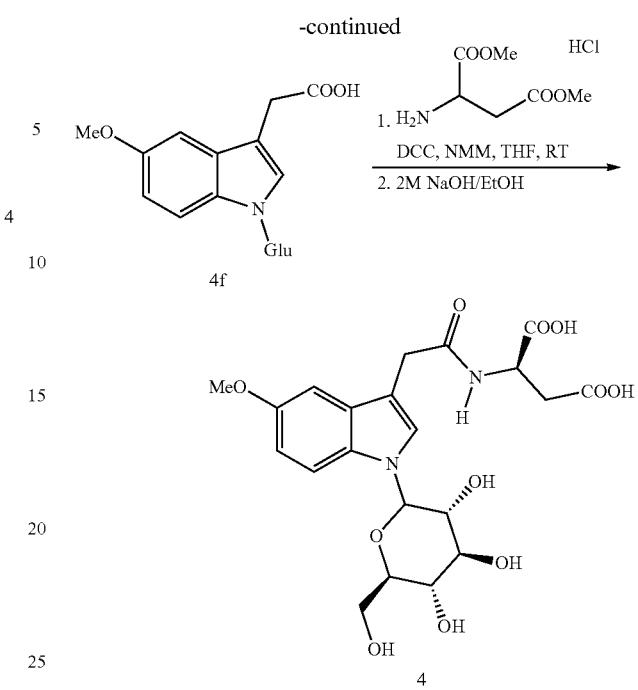

Step 1: Preparation of ethyl 2-(5-methoxy-1H-indol-3-yl)acetate (4b)

2.0 g of 5-methoxyindoleacetic acid was dissolved in 20 ml of DMF, and then $K_2CO_3$ (1.2 equivalent) was added thereto. The resulting mixture was stirred at room temperature for 30 minutes, and then added slowly with EtBr (1.2 equivalent) dropwise. After completion of the addition, the reaction mixture was stirred and refluxed for 4 hours. The reaction solution was then filtered and the filtrate was concentrated under reduced pressure. The residues were purified by column chromatography with petroleum ether:ethyl acetate 5:1 as the eluent to obtain the compound 4b (2.04 g, yield: 90%).

Step 2: Preparation of ethyl 2-(5-methoxyindolin-3-yl)acetate (4c)

2.04 g of compound 4b was dissolved in 10 ml of a mixed solution of concentrated hydrochloric acid-ethanol (1:1), and slowly added with 5.0 equivalent of pyridinium-borane ($BH_3.Py$) solution at 0° C. The reaction solution was warmed to room temperature, and stirred for 1 hour. The reaction solution was concentrated under reduced pressure. The residues were added with 60 ml of 10% sodium carbonate aqueous solution to adjust the pH to 8, and extracted with 80 ml of ethyl acetate three times. The ethyl acetate layer was separated, and purified by column chromatography with petroleum ether:ethyl acetate 5:1 as the eluent to obtain the title compound 4c (1.03 g, yield: 50%).

Step 3: Preparation of ethyl 2-(1-((2R,3R,4S,5S,6R)-3,4,5-trihydroxy-6-(hydroxymethyl)tetrahydro-2H-pyran-2-yl) 5-methoxyindolin-3-yl)acetate (4d)

1.03 g of compound 4c was dissolved in 5 ml of anhydrous ethanol. The reaction solution was added with D-glucose (1.2 equivalent), and refluxed for 5 hours. The reaction solution was filtered. The filtrate was purified by silica gel column chromatography with dichloromethane:methanol 10:1 as the eluent to obtain the compound 4d (1.16 g, yield: 73%).

Step 4: Preparation of ethyl 2-(1-((2R,3R,4S,5 S,6R)-3,4,5-trihydroxy-6-(hydroxymethyl)tetrahydro-2H-pyran-2-yl) 5-methoxy-1H-indol-3-yl) acetate (4e)

1.16 g of compound 4d was dissolved in 5 ml of toluene. The reaction solution was added with 1.1 equivalent of DDQ, and stirred at room temperature for 24 hours. The reaction solution was filtered. The filtrate was purified by silica gel column chromatography with dichloromethane:methanol 19:1 as the eluent to obtain the compound 4e (0.45 g, yield: 39%).

Step 5: Preparation of 2-(1-((2R,3R,4S,5 S,6R)-3,4,5-trihydroxy-6-(hydroxymethyl)tetrahydro-2H-pyran-2-yl)-5-methoxy-1H-indol-3-yl)acetic acid (4f)

0.45 g of compound 4e was dissolved in a sodium hydroxide-ethanol solution (2M), and the reaction solution was refluxed for 1 hour. After completion of the reaction, the pH was adjusted to 1-2 with hydrochloric acid, and the reaction solution was extracted with 20 ml of ethyl acetate twice. The organic phases were combined, dried over anhydrous sodium sulfate, and filtered. The filtrate was concentrated under reduced pressure. The residues were purified by silica gel column chromatography with dichloromethane:methanol 3:1 as the eluent to obtain the compound 4f (0.40 g, yield: 96%).

Step 6: Preparation of (2-(5-methoxy-1-((2R,3R,4S,5S,6R)-3,4,5-trihydroxy-6-hydroxymethyl)tetrahydro-2H-pyran-2-yl)-1H-indol-3-yl)acetyl)-D-aspartic acid (4)

0.40 g of compound 4f was dissolved in 4 ml of tetrahydrofuran. The reaction solution was added with methyl aspartate (1.5 equivalents), DCC (1.5 equivalents) and N-methylmorpholine (1.5 equivalents), and stirred at room temperature for 8 hours.

After completion of the reaction, the reaction solution was concentrated under reduced pressure. 5 ml of a 2M NaOH/EtOH solution was then added to the residue, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 4 as a white solid (0.45 g, yield: 85%).

Example 5 Preparation of (2-(5-chloro-1-((2R,3R,4S,5S,6R)-3,4,5-trihydroxy-6-(hydroxymethyl)tetrahydro-2H-pyran-2-yl)-1H-indol-3-yl)acetyl)-D-aspartic acid

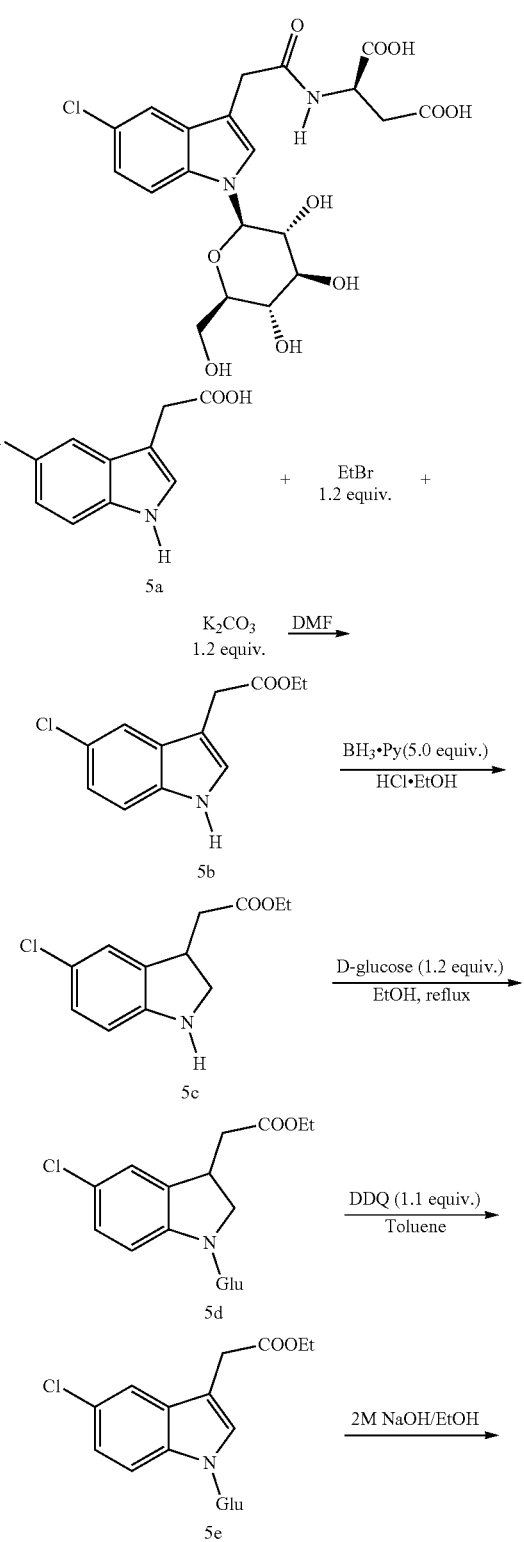

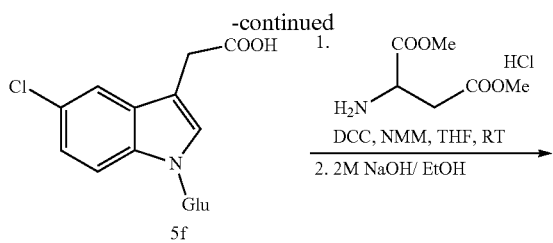

Step 1: Preparation of ethyl 2-(5-chloro-1H-indol-3-yl)acetate (5b)

2.0 g of 5-chloroindoleacetic acid was dissolved in 20 ml of DMF, and then $K_2CO_3$ (1.2 equivalent) was added thereto. The resulting mixture was stirred at room temperature for 30 minutes, and then added slowly with EtBr (1.2 equivalent) dropwise. After completion of the addition, the reaction mixture was stirred and refluxed for 4 hours. The reaction solution was then filtrated, concentrated under reduced pressure, and the residues were purified by column chromatography with petroleum ether:ethyl acetate 5:1 as the eluent to obtain the compound 5b (2.10 g, yield: 93%).

Step 2: Preparation of ethyl 2-(5-chloroindolin-3-yl)acetate (5c)

2.10 g of compound 5b was dissolved in 10 ml of a mixed solution of concentrated hydrochloric acid-ethanol (1:1), and slowly added with 5.0 equivalent of pyridinium-borane ($BH_3$.Py) solution at 0° C. The reaction solution was warmed to room temperature, and stirred for 1 hour. The reaction solution was concentrated under reduced pressure. The residues were added with 60 ml of 10% sodium carbonate aqueous solution to adjust the pH to 8, and extracted with 80 ml of ethyl acetate for three times. The ethyl acetate layer was separated, and purified by column chromatography with petroleum ether:ethyl acetate 5:1 as the eluent to obtain the title compound 5c (0.98 g, yield: 46%).

Step 3: Preparation of ethyl 2-(1-((2R,3R,4S,5S,6R)-3,4,5-trihydroxy-6-(hydroxymethyl)tetrahydro-2H-pyran-2-yl) 5-chloroindolin-3-yl)acetate (5d)

0.98 g of compound 5c was dissolved in 5 ml of anhydrous ethanol. The reaction solution was added with D-glucose (1.2 equivalent), and refluxed for 5 hours. The reaction solution was filtered. The filtrate was purified by silica gel column chromatography with dichloromethane:methanol 10:1 as the eluent to obtain the compound 5d (1.05 g, yield: 70%).

Step 4: Preparation of ethyl 2-(1-((2R,3R,4S,5S,6R)-3,4,5-trihydroxy-6-(hydroxymethyl)tetrahydro-2H-pyran-2-yl) 5-chloro-1H-indol-3-yl)acetate (5e)

1.05 g of compound 5d was dissolved in 5 ml of toluene. The reaction solution was added with 1.1 equivalent of DDQ, and stirred at room temperature for 24 hours. The reaction solution was filtered. The filtrate was purified by silica gel column chromatography with dichloromethane:methanol 19:1 as the eluent to obtain the compound 5e (0.43 g, yield: 41%).

Step 5: Preparation of 2-(1-((2R,3R,4S,5S,6R)-3,4,5-trihydroxy-6-(hydroxymethyl)tetrahydro-2H-pyran-2-yl)-5-chloro-1H-indol-3-yl)acetic acid (5f)

0.43 g of compound 5e was dissolved in a sodium hydroxide-ethanol solution (2M), and the reaction solution was refluxed for 1 hour. After completion of the reaction, the pH was adjusted to 1-2 with hydrochloric acid, and the reaction solution was extracted with 20 ml of ethyl acetate twice. The organic phases were combined, dried over anhydrous sodium sulfate, and filtered. The filtrate was concentrated under reduced pressure. The residues were purified by silica gel column chromatography with dichloromethane:methanol 3:1 as the eluent to obtain the compound 5f (0.38 g, yield: 96%).

Step 6: Preparation of (2-(5-chloro-1-((2R,3R,4S,5S,6R)-3,4,5-trihydroxy-6-hydroxymethyl)tetrahydro-2H-pyran-2-yl)-1H-indol-3-yl)acetyl)-D-aspartic acid (5)

0.38 g of compound 5f was dissolved in 4 ml of tetrahydrofuran. The reaction solution was added with methyl D-aspartate (1.5 equivalents), DCC (1.5 equivalents) and N-methylmorpholine (1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 5 as a white solid (0.45 g, yield: 88%).

Example 6 Preparation of (2-(5-bromo-1-((2R,3R,4S,5S,6R)-3,4,5-trihydroxy-6-(hydroxymethyl)tetrahydro-2H-pyran-2-yl)-1H-indol-3-yl)acetyl)-D-aspartic acid

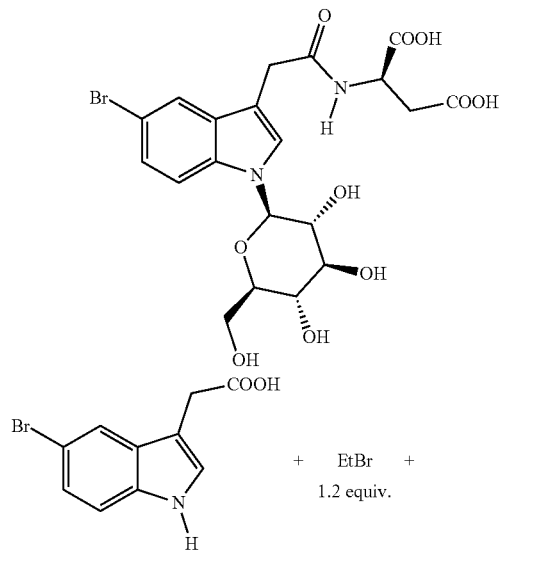

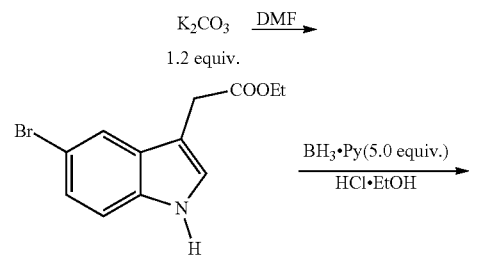

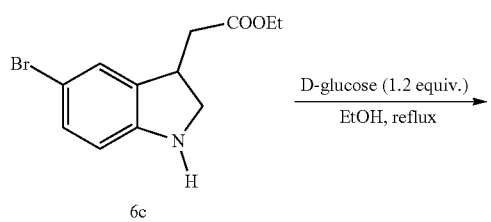

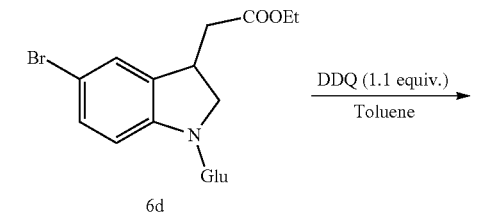

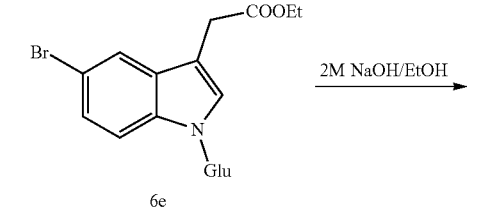

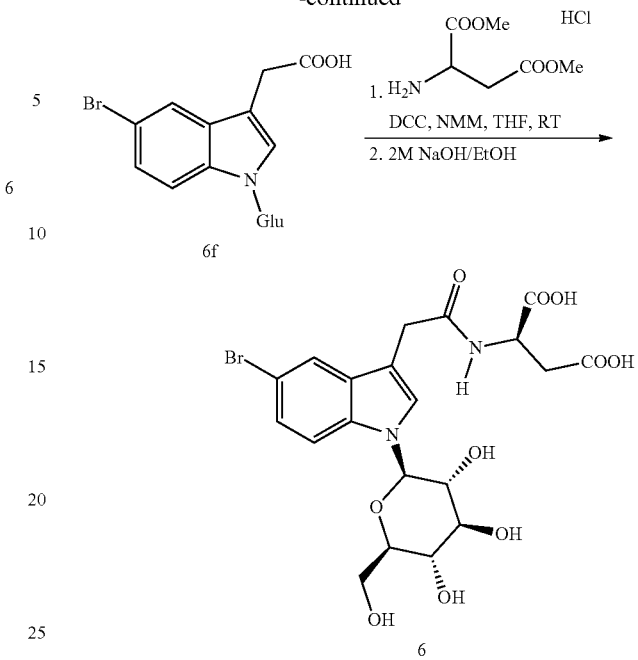

Step 1: Preparation of ethyl 2-(5-bromo-1H-indol-3-yl)acetate (6b)

2.0 g of 5-bromoindoleacetic acid was dissolved in 20 ml of DMF, and then $K_2CO_3$ (1.2 equivalent) was added thereto. The resulting mixture was stirred at room temperature for 30 minutes, and then added slowly with EtBr (1.2 equivalent) dropwise. After completion of the addition, the reaction mixture was stirred and refluxed for 4 hours. The reaction solution was then filtered and the filtrate was concentrated under reduced pressure. The residues were purified by column chromatography with petroleum ether:ethyl acetate 5:1 as the eluent to obtain the compound 6b (2.16 g, yield: 97%).

Step 2: Preparation of ethyl 2-(5-bromoindolin-3-yl)acetate (6c)

2.16 g of compound 6b was dissolved in 10 ml of a mixed solution of concentrated hydrochloric acid-ethanol (1:1), and slowly added with 5.0 equivalent of pyridinium-borane ($BH_3$.Py) solution at 0° C. The reaction solution was warmed to room temperature, and stirred for 1 hour. The reaction solution was concentrated under reduced pressure. The residues were added with 60 ml of 10% sodium carbonate aqueous solution to adjust the pH to 8, and extracted with 80 ml of ethyl acetate three times. The ethyl acetate layer was separated, and purified by column chromatography with petroleum ether:ethyl acetate 5:1 as the eluent to obtain the title compound 6c (0.81 g, yield: 37%).

Step 3: Preparation of ethyl 2-(1-((2R,3R,4S,5S,6R)-3,4,5-trihydroxy-6-(hydroxymethyl)tetrahydro-2H-pyran-2-yl) 5-bromoindolin-3-yl)acetate (6d)

0.81 g of compound 6c was dissolved in 5 ml of anhydrous ethanol. The reaction solution was added with D-glucose (1.2 equivalent), and refluxed for 5 hours. The reaction solution was filtered, and the filtrate was mixed with silica gel, and purified by silica gel column chromatography with dichloromethane:methanol 10:1 as the eluent to obtain the compound 6d (0.80 g, yield: 67%).

Step 4: Preparation of ethyl 2-(1-((2R,3R,4S,5 S,6R)-3,4,5-trihydroxy-6-(hydroxymethyl)tetrahydro-2H-pyran-2-yl) 5-bromo-1H-indol-3-yl)acetate (6e)

0.80 g of compound 6d was dissolved in 5 ml of toluene. The reaction solution was added with 1.1 equivalent of DDQ, and stirred at room temperature for 24 hours. The reaction solution was filtered. The filtrate was purified by silica gel column chromatography with dichloromethane:methanol 19:1 as the eluent to obtain the compound 6e (0.37 g, yield: 46%).

Step 5: Preparation of 2-(1-((2R,3R,4S,5 S,6R)-3,4,5-trihydroxy-6-(hydroxymethyl)tetrahydro-2H-pyran-2-yl)-5-bromo-1H-indol-3-yl)acetic acid (6f)

0.36 g of compound 6e was dissolved in a sodium hydroxide-ethanol solution (2M), and the reaction solution was refluxed for 1 hour. After completion of the reaction, the pH was adjusted to 1-2 with hydrochloric acid, and the reaction solution was extracted with 20 ml of ethyl acetate twice. The organic phases were combined, dried over anhydrous sodium sulfate, and filtered. The filtrate was concentrated under reduced pressure. The residues were purified by silica gel column chromatography with dichloromethane:methanol 3:1 as the eluent to obtain the compound 6f (0.33 g, yield: 98%).

Step 6: Preparation of (2-(5-bromo-1-((2R,3R,4S, 5S,6R)-3,4,5-trihydroxy-6-hydroxymethyl)tetrahydro-2H-pyran-2-yl)-1H-indol-3-yl)acetyl)-D-aspartic acid (6)

0.33 g of compound 6f was dissolved in 4 ml of tetrahydrofuran. The reaction solution was added with methyl D-aspartate (1.5 equivalents), DCC (1.5 equivalents) and N-methylmorpholine (1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 6 as a white solid (0.39 g, yield: 91%).

Example 7 Preparation of (2-(7-methyl-1-((2R,3R, 4S,5S,6R)-3,4,5-trihydroxy-6-hydroxymethyl)tetrahydro-2H-pyran-2-yl)-1H-indol-3-yl)acetyl)-D-aspartic acid

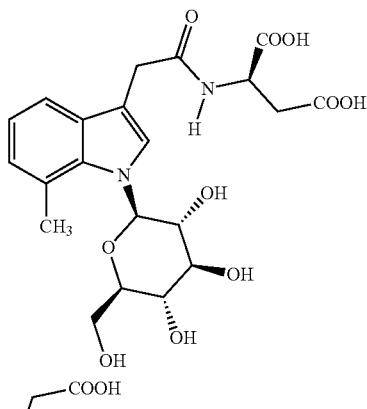

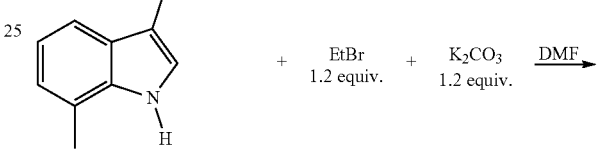

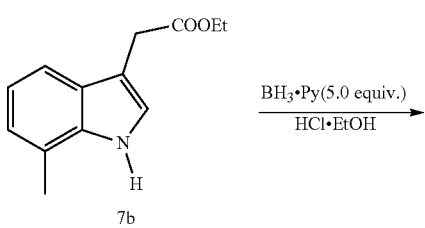

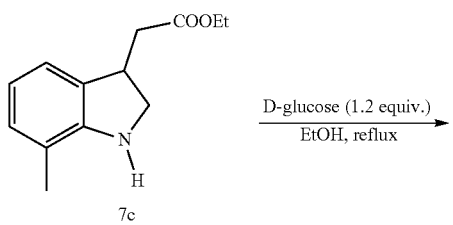

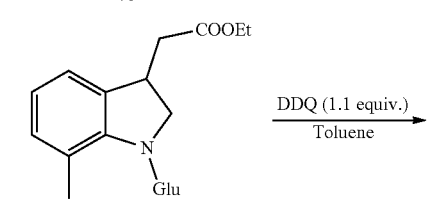

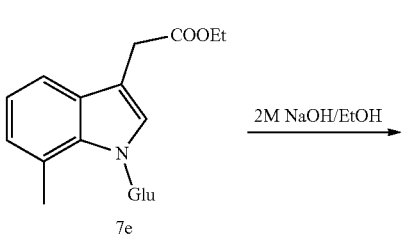

-continued

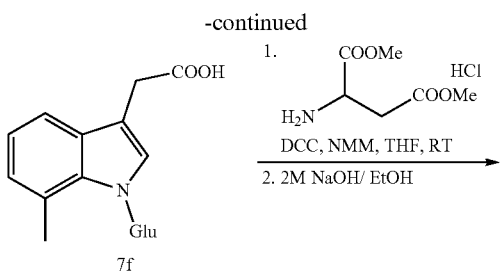

7f

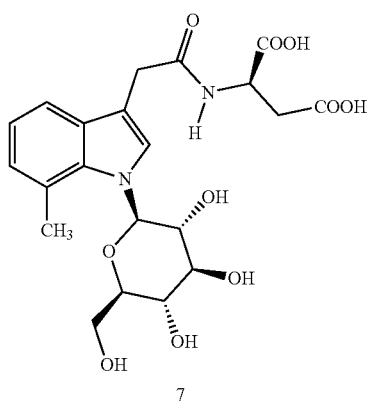

7

Step 1: Preparation of ethyl 2-(7-methyl-1H-indol-3-yl)acetate (7b)

2.0 g of 7-methylindoleacetic acid was dissolved in 20 ml of DMF, and then K$_2$CO$_3$ (1.2 equivalent) was added thereto. The resulting mixture was stirred at room temperature for 30 minutes, and then added slowly with EtBr (1.2 equivalent) dropwise. After completion of the addition, the reaction mixture was stirred and refluxed for 4 hours. The reaction solution was then filtered, concentrated under reduced pressure, and the residues were purified by column chromatography with petroleum ether:ethyl acetate 5:1 as the eluent to obtain the compound 7b (2.00 g, yield: 87%).

Step 2: Preparation of ethyl 2-(7-methylindolin-3-yl)acetate (7c)

2.00 g of compound 7b was dissolved in 10 ml of a mixed solution of concentrated hydrochloric acid-ethanol (1:1), and slowly added with 5.0 equivalent of pyridinium-borane (BH$_3$.Py) solution at 0° C. The reaction solution was warmed to room temperature, and stirred for 1 hour. The reaction solution was concentrated under reduced pressure. The residues were added with 60 ml of 10% sodium carbonate aqueous solution to adjust the pH to 8, and extracted with 80 ml of ethyl acetate three times. The ethyl acetate layer was separated, and purified by column chromatography with petroleum ether:ethyl acetate 5:1 as the eluent to obtain the title compound 7c (1.11 g, yield: 55%).

Step 3: Preparation of ethyl 2-(1-((2R,3R,4S,5S,6R)-3,4,5-trihydroxy-6-(hydroxymethyl)tetrahydro-2H-pyran-2-yl) 7-methylindolin-3-yl)acetate (7d)

1.11 g of compound 7c was dissolved in 5 ml of anhydrous ethanol. The reaction solution was added with D-glucose (1.2 equivalent), and refluxed for 5 hours. The reaction solution was filtered. The filtrate was purified by silica gel column chromatography with dichloromethane:methanol 10:1 as the eluent to obtain the compound 7d (1.11 g, yield: 63%).

Step 4: Preparation of ethyl 2-(1-((2R,3R,4S,5S,6R)-3,4,5-trihydroxy-6-(hydroxymethyl)tetrahydro-2H-pyran-2-yl) 7-methyl-1H-indol-3-yl)acetate (7e)

1.11 g of compound 7d was dissolved in 5 ml of toluene. The reaction solution was added with 1.1 equivalent of DDQ, and stirred at room temperature for 24 hours. The reaction solution was filtered. The filtrate was purified by silica gel column chromatography with dichloromethane:methanol 19:1 as the eluent to obtain the compound 7e (0.44 g, yield: 40%).

Step 5: Preparation of 2-(1-((2R,3R,4S,5S,6R)-3,4,5-trihydroxy-6-(hydroxymethyl)tetrahydro-2H-pyran-2-yl)-7-methyl-1H-indol-3-yl)acetic acid (7f)

0.44 g of compound 7e was dissolved in a sodium hydroxide-ethanol solution (2M), and the reaction solution was refluxed for 1 hour. After completion of the reaction, the pH was adjusted to 1-2 with hydrochloric acid, and the reaction solution was extracted with 20 ml of ethyl acetate twice. The organic phases were combined, dried over anhydrous sodium sulfate, and filtered. The filtrate was concentrated under reduced pressure. The residues were purified by silica gel column chromatography with dichloromethane:methanol 3:1 as the eluent to obtain the compound 7f (0.39 g, yield: 95%).

Step 6: Preparation of (2-(7-methyl-1-((2R,3R,4S,5S,6R)-3,4,5-trihydroxy-6-hydroxymethyl)tetrahydro-2H-pyran-2-yl)-1H-indol-3-yl)acetyl)-D-aspartic acid (7)

0.39 g of compound 7f was dissolved in 4 ml of tetrahydrofuran. The reaction solution was added with methyl D-aspartate (1.5 equivalents), DCC (1.5 equivalents) and N-methylmorpholine (1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 7 as a white solid (0.47 g, yield: 89%).

Example 8 Preparation of (2-(7-methoxy-1-((2R,3R,4S,5S,6R)-3,4,5-trihydroxy-6-hydroxymethyl)tetrahydro-2H-pyran-2-yl)-1H-indol-3-yl)acetyl)-D-aspartic acid

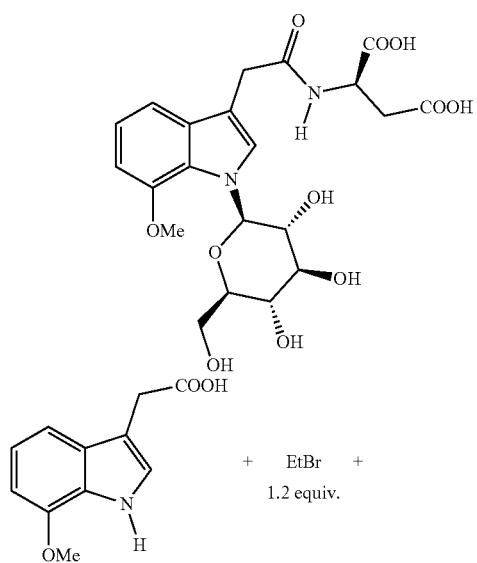

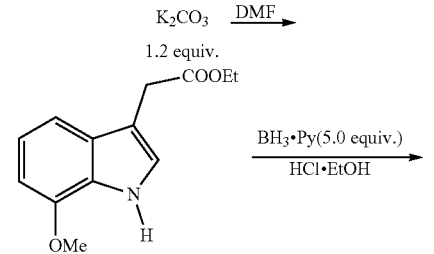

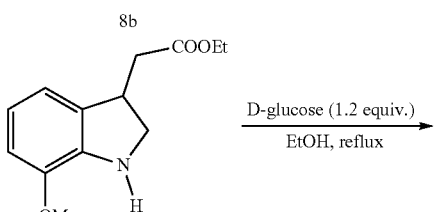

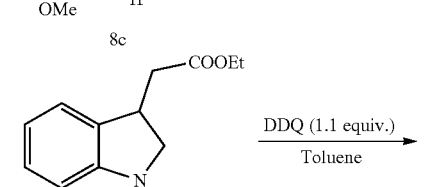

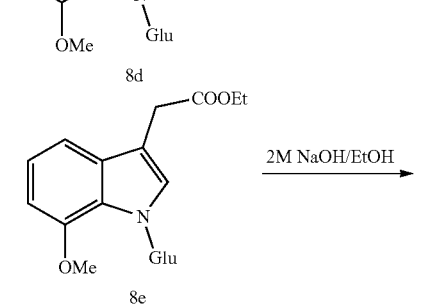

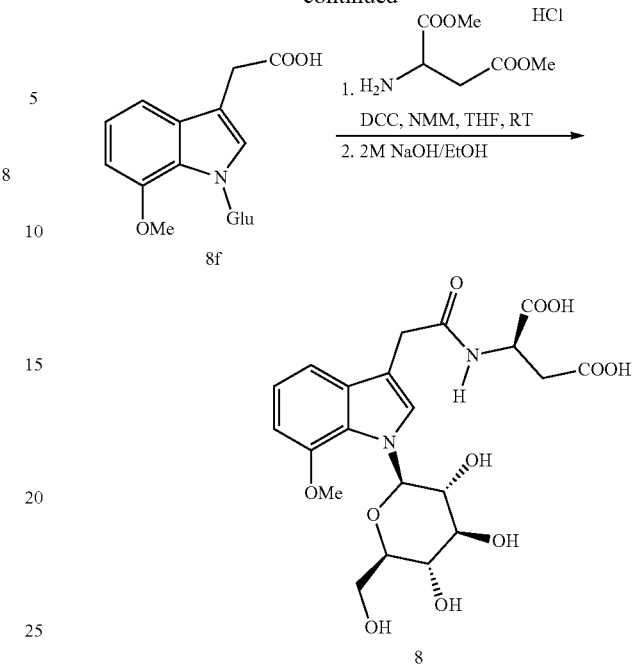

Step 1: Preparation of ethyl 2-(7-methoxy-1H-indol-3-yl)acetate (8b)

2.0 g of 7-methoxyindoleacetic acid was dissolved in 20 ml of DMF, and then $K_2CO_3$ (1.2 equivalent) was added thereto. The resulting mixture was stirred at room temperature for 30 minutes, and then added slowly with EtBr (1.2 equivalent) dropwise. After completion of the addition, the reaction mixture was stirred and refluxed for 4 hours. The reaction solution was then filtrated, concentrated under reduced pressure, and the residues were purified by column chromatography with petroleum ether:ethyl acetate 5:1 as the eluent to obtain the compound 8b (2.06 g, yield: 91%).

Step 2: Preparation of ethyl 2-(7-methoxyindolin-3-yl)acetate (8c)

2.06 g of compound 8b was dissolved in 10 ml of a mixed solution of concentrated hydrochloric acid-ethanol (1:1), and slowly added with 5.0 equivalent of pyridinium-borane ($BH_3$.Py) solution at 0° C. The reaction solution was warmed to room temperature, and stirred for 1 hour. The reaction solution was concentrated under reduced pressure. The residues were added with 60 ml of 10% sodium carbonate aqueous solution to adjust the pH to 8, and extracted with 80 ml of ethyl acetate three times. The ethyl acetate layer was separated, and purified by column chromatography with petroleum ether:ethyl acetate 5:1 as the eluent to obtain the title compound 8c (1.00 g, yield: 48%).

Step 3: Preparation of ethyl 2-(1-((2R,3R,4S,5S,6R)-3,4,5-trihydroxy-6-(hydroxymethyl)tetrahydro-2H-pyran-2-yl) 7-methoxyindolin-3-yl)acetate (8d)

1.00 g of compound 8c was dissolved in 5 ml of anhydrous ethanol. The reaction solution was added with D-glucose (1.2 equivalent), and refluxed for 5 hours. The reaction solution was filtered. The filtrate was purified by silica gel column chromatography with dichloromethane:methanol 10:1 as the eluent to obtain the compound 8d (1.16 g, yield: 75%).

Step 4: Preparation of ethyl 2-(1-((2R,3R,4S,5 S,6R)-3,4,5-trihydroxy-6-(hydroxymethyl)tetra-hydro-2H-pyran-2-yl) 7-methoxy-1H-indol-3-yl) acetate (8e)

1.16 g of compound 8d was dissolved in 5 ml of toluene. The reaction solution was added with 1.1 equivalent of DDQ, and stirred at room temperature for 24 hours. The reaction solution was filtered. The filtrate was purified by silica gel column chromatography with dichloromethane:methanol 19:1 as the eluent to obtain the compound 8e (0.32 g, yield: 28%).

Step 5: Preparation of 2-(1-((2R,3R,4S,5 S,6R)-3,4,5-trihydroxy-6-(hydroxymethyl)tetrahydro-2H-pyran-2-yl)-7-methoxy-1H-indol-3-yl)acetic acid (8f)

0.32 g of compound 8e was dissolved in a sodium hydroxide-ethanol solution (2M), and the reaction solution was refluxed for 1 hour. After completion of the reaction, the pH was adjusted to 1-2 with hydrochloric acid, and the reaction solution was extracted with 20 ml of ethyl acetate twice. The organic phases were combined, dried over anhydrous sodium sulfate, and filtered. The filtrate was concentrated under reduced pressure. The residues were purified by silica gel column chromatography with dichloromethane:methanol 3:1 as the eluent to obtain the compound 8f (0.28 g, yield: 96%).

Step 6: Preparation of (2-(7-methoxy-1-((2R,3R,4S, 5S,6R)-3,4,5-trihydroxy-6-hydroxymethyl)tetra-hydro-2H-pyran-2-yl)-1H-indol-3-yl)acetyl)-D-aspartic acid (8)

0.28 g of compound 8f was dissolved in 4 ml of tetrahydrofuran. The reaction solution was added with methyl D-aspartate (1.5 equivalents), DCC (1.5 equivalents) and N-methylmorpholine (1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 8 as a white solid (0.33 g, yield: 86%).

Example 9 Preparation of (2-(5-methyl-1-((2R,3R, 4S,5S,6R)-3,4,5-trihydroxy-6-hydroxymethyl)tetra-hydro-2H-pyran-2-yl)-1H-indol-3-yl)acetyl)-D-glutamic acid

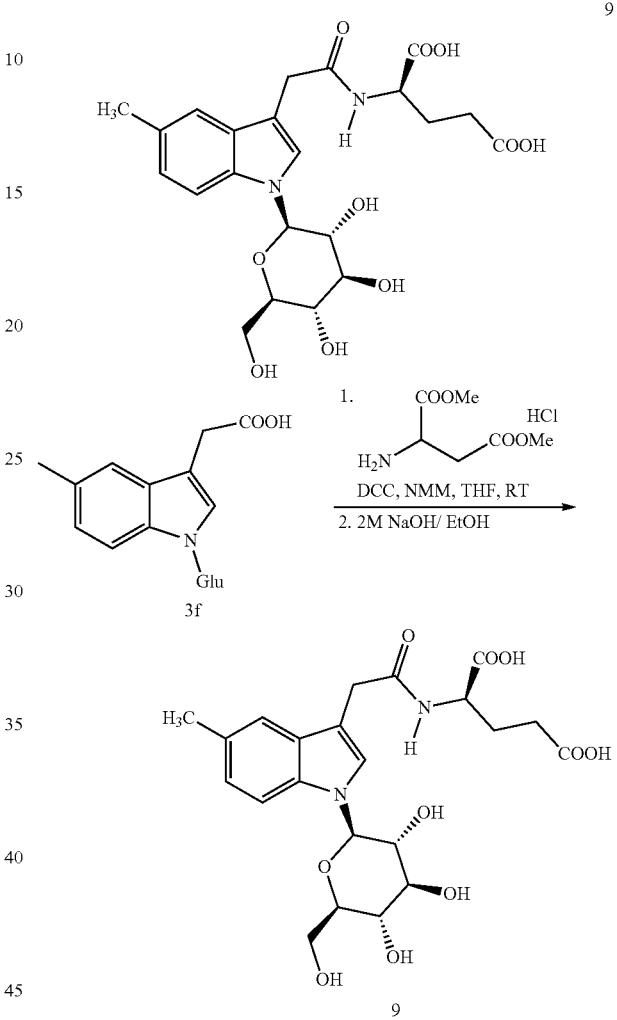

Step 1: Preparation of (2-(5-methyl-1-((2R,3R,4S, 5S,6R)-3,4,5-trihydroxy-6-hydroxymethyl)tetra-hydro-2H-pyran-2-yl)-1H-indol-3-yl)acetyl)-D-glutamic acid (9)

0.43 g of compound 3f was dissolved in 4 ml of tetrahydrofuran. The reaction solution was added with methyl D-glutamate (1.5 equivalents), DCC (1.5 equivalents) and N-methylmorpholine (1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 9 as a white solid (0.53 g, yield: 87%).

Example 10 Preparation of (2-(5-chloro-1-((2R,3R, 4S,5S,6R)-3,4,5-trihydroxy-6-hydroxymethyl)tetrahydro-2H-pyran-2-yl)-1H-indol-3-yl)acetyl)-D-glutamic acid

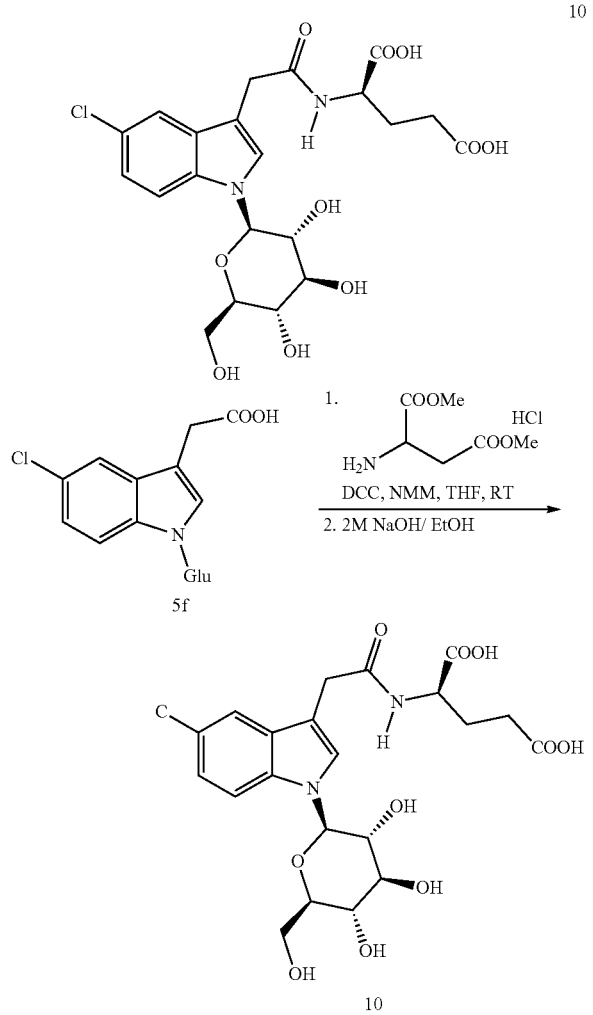

Step 1: Preparation of (2-(5-chloro-1-((2R,3R,4S, 5S,6R)-3,4,5-trihydroxy-6-hydroxymethyl)tetrahydro-2H-pyran-2-yl)-1H-indol-3-yl)acetyl)-D-glutamic acid (10)

0.38 g of compound 5f was dissolved in 4 ml of tetrahydrofuran. The reaction solution was added with methyl D-glutamate (1.5 equivalents), DCC (1.5 equivalents) and N-methylmorpholine (1.5 equivalents), and stirred at room temperature for 8 hours. After completion of the reaction, the reaction solution was concentrated under reduced pressure. 5 ml of a 2M NaOH/EtOH solution was then added to the residues, and the reaction solution was refluxed for 1 hour. After completion of the reaction, the pH was adjusted to 5 with hydrochloric acid, and the reaction solution was extracted with 10 ml of ethyl acetate twice. The organic phases were combined, dried over anhydrous sodium sulfate, and filtered. The filtrate was concentrated under reduced pressure. The residues were purified by column chromatography with dichloromethane:methanol 5:1 as the eluent to obtain the title product 10 as a white solid (0.45 g, yield: 86%).

Test Example 1 Aqueous Ammonia-Induced Cough Test

Test animals: Kunming mice (body weight 18-22 g, half male and half female), purchased from Beijing Vital River Laboratory Animal Technology Co., Ltd., with Certificate No.: SCXK-(Beijing)2012-001.

Test reagent: Codeine phosphate (Europharm Laboratoires Co., Ltd.).

Device: YC-Y800 Medical ultrasonic nebulizer (Beijing Yadu Technology Co., Ltd., with Beijing Pharmaceutical Supervision Certificate No.: Beijing 99 No. 223145); UV-2450 UV-visible spectrophotometer (Shimadzu Co., Japan); UX420S Animal balance (Shimadzu Co., Japan); and milli electronic balance (Sartorius Co., Germany).

Test Method:

The mice were adaptively fed for 3 days followed by screening. The ultrasonic nebulizer was preheated, and added with 40 ml of fresh aqueous ammonia solution (12.5%). The mice were placed in 1000 ml beaker. The beaker's mouth was sealed with a plastic wrap with two holes opened (one for inserting the ultrasonic atomizer outlet tube, and the other for ventilation). Ammonia was continuously introduced by the ultrasonic atomizer at its minimal power for 60 seconds, followed by stopping the ultrasonic atomizer immediately. The plastic wrap was quickly opened to allow the ammonia to diffuse naturally. Mice which coughed for less than 10 times or more than 80 times within three minutes were excluded. The qualified mice were randomly grouped into blank control group, compound of the present invention group, and codeine phosphate-positive control group. The above groups were intragastrically administrated with the drugs according to body weight, and the blank control group was administrated with equal volume of distilled water. The administration was carried out once a day for five consecutive days. The mice were placed one by one in an inverted 5 L sealed glass bell jar for one hour after the last administration, and treated by a constant pressure ammonia spray stimulation for 15 seconds (10 mL of ammonia spray/time for one mouse, and changed each time). After the stimulation stopped, the mice were taken out to observe the latent period of the cough of the mice (the time from spraying starting to coughing starting) and the number of coughs within 2 minutes (cough was identified by severely contracting the abdominal muscles and opening the mouth, with a slight cough sound sometimes).

Statistical method: data analysis of the experimental data was carried out with SPSS 10.0 statistical software, and t-test was used for comparison between groups.

The doses of the compound of the present invention and codeine phosphate and the observation results are shown in Table 1 below.

TABLE 1

Antitussive effect of the compound of the present invention on the aqueous ammonia-induced cough in mice ($\bar{x} \pm s$)

| Test groups | Dose (mg · kg$^{-1}$) | Number of animals (n) | Latentperiod (s) | Number of coughs (times/2 min) |
|---|---|---|---|---|
| Blank control group | — | 16 | 33.2 ± 17.4 | 30.2 ± 9.6 |
| Compound 1 | 20 | 16 | 45.8 ± 8.2** | 19.1 ± 10.7* |
| Compound 2 | 20 | 16 | 48.5 ± 9.4** | 17.3 ± 4.6** |
| Compound 3 | 20 | 16 | 38.1 ± 5.3* | 20.7 ± 5.2* |
| Compound 4 | 20 | 16 | 40.3 ± 5.5** | 18.5 ± 4.3** |
| Compound 5 | 20 | 16 | 42.6 ± 11.2* | 19.6 ± 5.1** |
| Compound 6 | 20 | 16 | 40.7 ± 5.2** | 21.8 ± 7.3* |
| Compound 7 | 20 | 16 | 42.1 ± 7.2* | 18.6 ± 8.5** |
| Compound 8 | 20 | 16 | 39.6 ± 5.5** | 19.2 ± 4.7** |
| Compound 9 | 20 | 16 | 38.1 ± 4.7* | 23.8 ± 5.1* |
| Compound 10 | 20 | 16 | 39.4 ± 4.1** | 19.4 ± 6.3** |
| Codeine phosphate | 15 mL · kg$^{-1}$ | 16 | 48.3 ± 5.9** | 14.2 ± 6.5** |

Note:
Compared with the blank control group,
*P < 0.05,
**P < 0.01.

Conclusion: As can be seen from Table 1, the compound of the present invention has a significant inhibition effect on aqueous ammonia-induced cough in mice. It can prolong the cough-inducing latentperiod and reduce the number of coughs, which have a statistically significant difference compared with the blank control group. The efficacy is similar to the positive control drug codeine phosphate.

Test Example 2 Citric Acid-Induced Cough Test

Test animals: Guinea pigs (body weight 180-220 g, half male and half female), purchased from Beijing Vital River Laboratory Animal Technology Co., Ltd.

Test reagent: Codeine phosphate (Europharm Laboratoires Co., Ltd.).

The devices are the same as in Test Example 1.

Test Method:

The guinea pigs were adaptively fed for 1 day followed by preliminary screening.

The guinea pigs were placed one by one in an inverted 5 L sealed glass bell jar, and treated by a constant pressure spray stimulation (17.5% citric acid solution) for one minute. The number of coughs within 5 minutes from the spray was recorded, and the guinea pigs which coughed more than 10 times were chosen as qualified test animals. The qualified guinea pigs were randomly grouped into blank control group, compound of the present invention group, and codeine phosphate-positive control group. The above groups were intragastrically administrated with the drugs according to body weight, and the blank control group was administrated with equal volume of distilled water. The intragastrical administration was carried out for five consecutive days. The guinea pigs were placed in an inverted 5 L sealed glass bell jar for one hour after the last administration, and treated by the nebulizer for 30 seconds. The latentperiod of the cough of the guinea pigs (the time from starting spraying of 17.5% citric acid to coughing starting) and the number of coughs within 5 minutes were observed.

Statistical method: data analysis of the experimental data was carried out with SPSS 10.0 statistical software, and t-test was used for comparison between groups.

The doses of the compound of the present invention and codeine phosphate and the observation results are shown in Table 2 below.

TABLE 2

Antitussive effect of the compound of the present invention on the citric acid-induced cough in guinea pigs ($\bar{x} \pm s$)

| Test groups | Dose (mg · kg$^{-1}$) | Number of animals (n) | Latentperiod (s) | Number of coughs (times/2 min) |
|---|---|---|---|---|
| Blank control group | — | 18 | 53 ± 37 | 21 ± 9 |
| Compound 1 | 20 | 18 | 147 ± 89** | 10 ± 10* |
| Compound 2 | 20 | 14 | 98 ± 59 | 9 ± 4** |
| Compound 3 | 20 | 18 | 128 ± 65** | 9 ± 5** |
| Compound 4 | 20 | 15 | 120 ± 55** | 10 ± 4** |
| Compound 5 | 20 | 16 | 110 ± 32* | 10 ± 5** |
| Compound 6 | 20 | 15 | 127 ± 52** | 9 ± 7** |
| Compound 7 | 20 | 16 | 130 ± 22** | 8 ± 8** |
| Compound 8 | 20 | 13 | 110 ± 32** | 10 ± 4** |
| Compound 9 | 20 | 17 | 121 ± 47** | 9 ± 5** |
| Compound 10 | 20 | 16 | 139 ± 41** | 10 ± 6** |
| Codeine phosphate | 15 mL · kg$^{-1}$ | 18 | 107 ± 41* | 12 ± 6* |

Note:
Compared with the blank control group,
*P < 0.05,
**P < 0.01.

Conclusion: As can be seen from Table 2, the compound of the present invention has a significant inhibition effect on citric acid-induced cough in mice. It can prolong the cough-inducing latentperiod and reduce the number of coughs, which have a statistically significant difference compared with the blank control group. The efficacy is superior to the positive control drug codeine phosphate.

Test Example 3 Phlegm-Reducing Effect of the Compound of the Present Invention

Test animals: Kunming mice (body weight 18-22 g, half male and half female), purchased from Beijing Vital River Laboratory Animal Technology Co., Ltd.

Test reagent: Ammonium chloride (Guangzhou Chemical Reagent Factory).

The devices were the same as in Test Example 1.

Test Method:

According to the method of LI Yikui's phlegm-reducing test, the mice were fed normally for 3 days, and then randomly grouped into blank control group, compound of the present invention group, and ammonium chloride-positive control group. The mice in each group were intragastrically administrated with equal volume of drugs or distilled water for five consecutive days. 2.5% phenol red was intraperitoneally injected in 0.1 mL/10 g 30 minutes after the last administration. The animals were sacrificed after 30 minutes, the tracheal section was separated and placed in a test tube containing physiological saline which was added with 0.1 mL of 1.0 mol/L sodium hydroxide then. The absorbance A value was measured at a wavelength of 546 nm using an UV-2450 spectrophotometer. The phenol red excretion amount was calculated from the phenol red standard curve, and the significance of the difference between the groups was compared.

Statistical method: data analysis of the experimental data was carried out with SPSS 10.0 statistical software, and t-test was used for comparison between groups.

The doses of the compound of the present invention and ammonium chloride and the observation results are shown in Table 3 below.

TABLE 3

Effect of the compound of the present invention on tracheal phenol red excretion amount in mice ($\bar{x} \pm s$)

| Test groups | Dose (mg · kg$^{-1}$) | Number of animals (n) | Tracheal phenol red excretion amount (mg · L$^{-1}$) |
|---|---|---|---|
| Blank control group | — | 16 | 0.468 ± 0.147 |
| Compound 1 | 20 | 16 | 1.125 ± 0.129** |
| Compound 2 | 20 | 16 | 0.988 ± 0.211** |
| Compound 3 | 20 | 16 | 0.971 ± 0.114** |
| Compound 4 | 20 | 16 | 1.072 ± 0.221** |
| Compound 5 | 20 | 16 | 0.831 ± 0.107* |
| Compound 6 | 20 | 16 | 0.888 ± 0.145** |
| Compound 7 | 20 | 16 | 0.956 ± 0.270** |
| Compound 8 | 20 | 16 | 1.142 ± 0.132** |
| Compound 9 | 20 | 16 | 1.089 ± 0.139**[1] |
| Compound 10 | 20 | 16 | 0.962 ± 0.101** |
| Ammonium chloride | 1000 | 16 | 1.068 ± 0.224* |

Note:
Compared with the blank control group,
*P < 0.05,
**P < 0.01.

Conclusion: As can be seen from Table 3, the compound of the present invention can significantly increase the phenol red excretion amount, and has a phlegm-reducing effect. It has a statistically significant difference compared with the blank control group.

The efficacy is similar to the positive control drug ammonium chloride.

Test Example 4 Effect of the compound of the present invention on asthma

Test animals: Guinea pigs (body weight 180-220 g, half male and half female), purchased from Beijing Vital River Laboratory Animal Technology Co., Ltd.

Test reagent: Aminophylline solution (Guangzhou Mingxing Pharmaceutical Co., Ltd.), histamine phosphate (Shanghai Kaiyang Biotechnology Co., Ltd.).

Device: 402AI ultrasonic nebulizer (Jiangsu Yuwell medical equipment & supply Co., Ltd.), 5000 ml glass cover, stopwatch.

Test Method:

The guinea pigs were adaptively fed for 1 day followed by preliminary screening. The guinea pigs were placed one by one in an inverted 5 L sealed glass bell jar, and histamine phosphate was sprayed at a constant pressure for 15 seconds after the guinea pigs were quiet. After the spray was stopped, the asthma-inducing latentperiod within 6 minutes was observed. Guinea pigs with asthmatic convulsion within 150 seconds were chosen as qualified test animals. The qualified guinea pigs were randomly grouped into blank control group, compound of the present invention group, and aminophylline-positive control group. The administration was carried out once a day for three consecutive days. The guinea pigs were inhaled with histamine phosphate one hour after the last administration, and the time when convulsions and tumble occurred was recorded as the latentperiod (the time from spraying starting to falling down). The observation was continued for 6 minutes, the latentperiod of guinea pigs that did not fall down within 6 minutes was recorded as 360 seconds. The latentperiod of the control group and the administration group was statistically compared.

Statistical method: data analysis of the experimental data was carried out with SPSS 10.0 statistical software, and t-test was used for comparison between groups.

The doses of the compound of the present invention and aminophylline and the observation results are shown in Table 4 below.

TABLE 4

Effect of the compound of the present invention on asthma induced by spray in guinea pigs ($\bar{x} \pm s$)

| Test groups | Dose (mg · kg$^{-1}$) | Number of animals (n) | Tracheal phenol red excretion amount (mg · L$^{-1}$) |
|---|---|---|---|
| Blank control group | — | 16 | 55.9 ± 9.74 |
| Compound 1 | 20 | 16 | 90.2 ± 26.33* |
| Compound 2 | 20 | 16 | 98.4 ± 36.13* |
| Compound 3 | 20 | 16 | 91.5 ± 28.02* |
| Compound 4 | 20 | 16 | 88.4 ± 32.45* |
| Compound 5 | 20 | 16 | 95.1 ± 26.93* |
| Compound 6 | 20 | 16 | 96.2 ± 18.33* |
| Compound 7 | 20 | 16 | 94.0 ± 29.01* |
| Compound 8 | 20 | 16 | 87.4 ± 15.23* |
| Compound 9 | 20 | 16 | 88.14 ± 32.22* |
| Compound 10 | 20 | 16 | 90.4 ± 16.56* |
| Aminophylline | 70 | 16 | 77.3 ± 17.6* |

Note:
Compared with the blank control group,
*P < 0.05,
**P < 0.01.

Conclusion: As can be seen from Table 4, the compound of the present invention can significantly prolong the latent-period, and has an antiasthmatic effect. It has a statistically significant difference compared with the blank control group. The efficacy is superior to the positive control drug aminophylline.

What is claimed is:

1. A compound of formula (I), or a mesomer, racemate, enantiomer, diastereomer thereof, or a mixture thereof, or a pharmaceutically acceptable salt thereof,

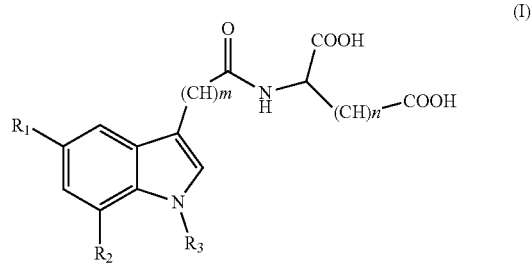

wherein,

R$_1$ is selected from the group consisting of hydrogen, halogen, hydroxy, amino, cyano, alkyl, alkoxy, haloalkyl, haloalkoxy and cycloalkyl;

R$_2$ is selected from the group consisting of hydrogen, halogen, alkyl, alkoxy, haloalkyl, haloalkoxy and cycloalkyl;

R$_3$ is pentose;

n is an integer from 1 to 4; and m is an integer from 1 to 4.

2. The compound according to claim 1, wherein R$_3$ is selected from the group consisting of ribose, deoxyribose and xylose.

3. The compound according to claim 1, wherein R$_3$ is selected from the group consisting of D-ribose, D-deoxyribose and D-xylose.

4. A method of treating a cough in a patient in need thereof, the method comprising administering to the patient a compound of formula (I), or a mesomer, racemate, enantiomer, diastereomer thereof, or a mixture thereof, or a pharmaceutically acceptable salt thereof,

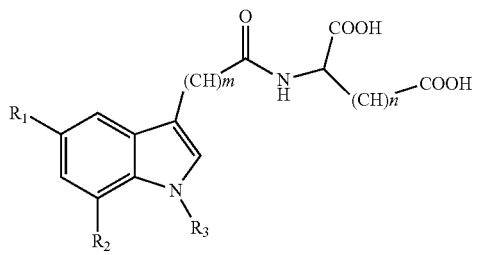

(I)

wherein, $R_1$ is selected from the group consisting of hydrogen, halogen, hydroxy, amino, cyano, alkyl, alkoxy, haloalkyl, haloalkoxy and cycloalkyl;

$R_2$ is selected from the group consisting of hydrogen, halogen, alkyl, alkoxy, haloalkyl, haloalkoxy and cycloalkyl;

$R_3$ is selected from the group consisting of pentose and hexose;

n is an integer from 1 to 4; and m is an integer from 1 to 4.

5. The method according to claim 4, wherein the compound of formula (I) is a compound of formula (II),

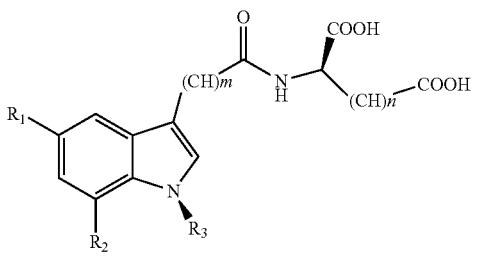

(II)

wherein, $R_1$, $R_2$, $R_3$, m and n are as defined in claim 1.

6. The method according to claim 4, wherein $R_1$ is selected from the group consisting of hydrogen, halogen, alkyl, alkoxy, haloalkyl and haloalkoxy.

7. The method according to claim 4, wherein $R_2$ is selected from the group consisting of hydrogen, halogen, $C_1$-$C_6$ alkyl and $C_1$-$C_6$ alkoxy.

8. The method according to claim 4, wherein $R_3$ is pentose.

9. The method according to claim 4, wherein $R_3$ is hexose.

10. The method according to claim 4, wherein m is 1 or 2.

11. The method according to claim 4, wherein n is 1 or 2.

12. The method according to claim 4, wherein the compound of formula (I) is selected from the group consisting of:

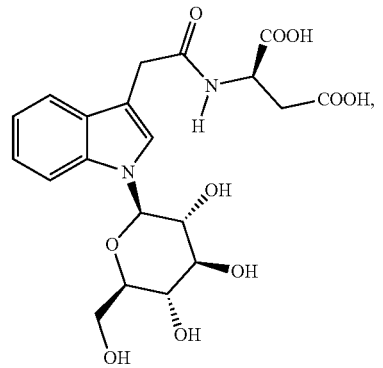

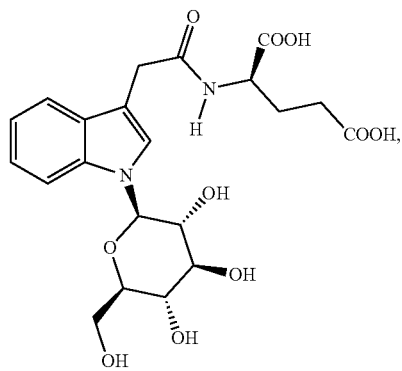

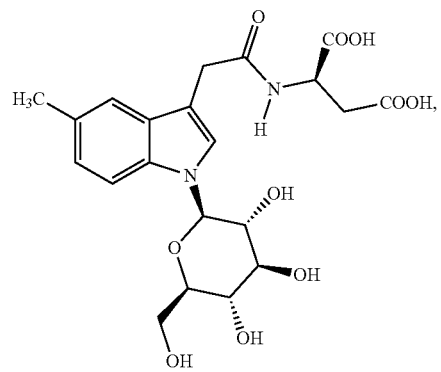

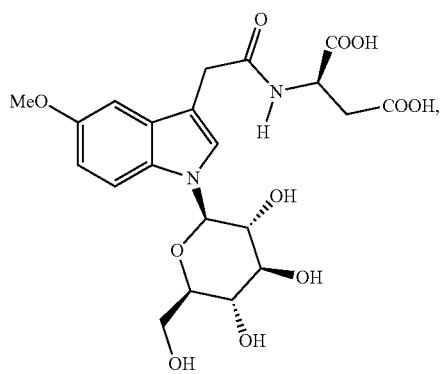

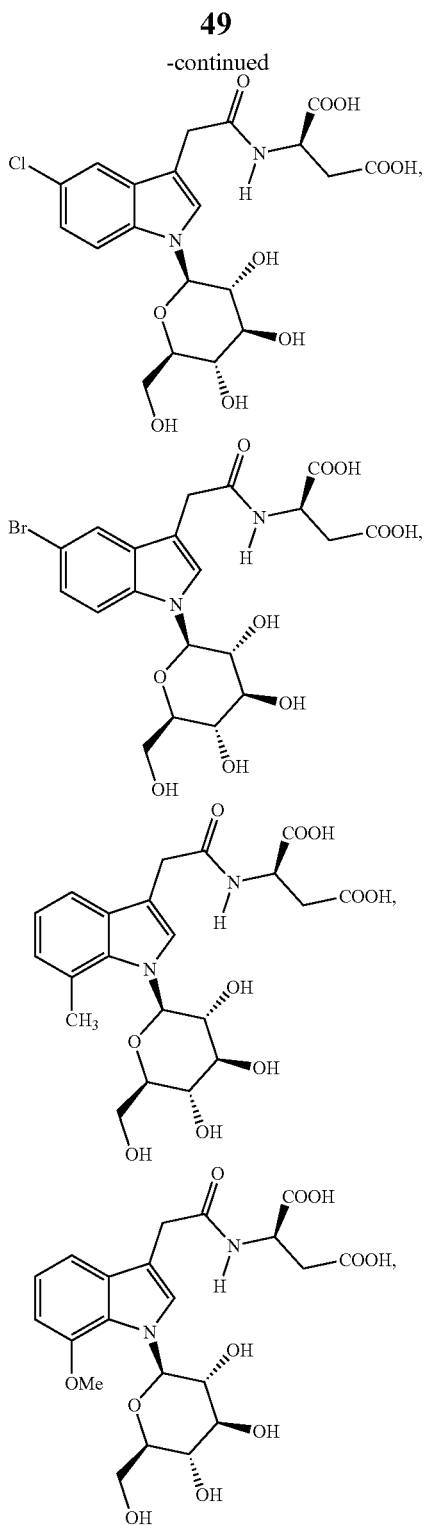

13. The method according to claim 4, wherein the pharmaceutically acceptable salt is a basic addition salt.

14. The method according to claim 4, wherein $R_3$ is selected from the group consisting of ribose, deoxyribose and xylose.

15. The method according to claim 4, wherein $R_3$ is selected from the group consisting of D-ribose, D-deoxyribose and D-xylose.

16. The method according to claim 4, wherein $R_3$ is selected from the group consisting of glucose, fructose and galactose.

17. The method according to claim 4, wherein $R_3$ is selected from the group consisting of D-glucose, D-fructose and D-galactose.

18. The method according to claim 4, wherein the pharmaceutically acceptable salt is sodium salt, potassium salt, calcium salt, magnesium salt, tetramethyl quaternary ammonium salt, tetraethyl quaternary ammonium salt, methylamine salt, dimethylamine salt, trimethylamine salt, triethylamine salt or ethylamine salt.

* * * * *